(12) United States Patent
Kronenberg et al.

(10) Patent No.: US 8,058,015 B2
(45) Date of Patent: Nov. 15, 2011

(54) MARKERS FOR CHRONIC KIDNEY DISEASE

(75) Inventors: Florian Kronenberg, Innsbruck (AT); Barbara Kollerits, Innsbruck (AT); Danilo Fliser, Heidelberg (DE)

(73) Assignee: Medizinische Universität Innsbruck, Innsbruck (AT)

( * ) Notice: Subject to any disclaimer, the term of this patent is extended or adjusted under 35 U.S.C. 154(b) by 0 days.

(21) Appl. No.: 12/523,625

(22) PCT Filed: Jan. 21, 2008

(86) PCT No.: PCT/EP2008/000420
§ 371 (c)(1),
(2), (4) Date: Feb. 9, 2010

(87) PCT Pub. No.: WO2008/089936
PCT Pub. Date: Jul. 31, 2008

(65) Prior Publication Data
US 2010/0143951 A1    Jun. 10, 2010

(30) Foreign Application Priority Data

Jan. 22, 2007    (EP) .................................. 07001340

(51) Int. Cl.
*G01N 33/53* (2006.01)
(52) U.S. Cl. ............................. 435/7.1; 435/7.2; 436/518
(58) Field of Classification Search ........................ None
See application file for complete search history.

(56) References Cited

U.S. PATENT DOCUMENTS
2005/0004348 A1    1/2005    Miyamoto et al. ........... 435/69.1

FOREIGN PATENT DOCUMENTS
WO    WO 02/08271    1/2002

OTHER PUBLICATIONS

Komaba et al. (Am J. Nephrol. 2006 vol. 26, p. 476-482).*
Haiman et al. (Kidney International. 2005 vol. 68, p. 1130-1136).*
Fliser et al., "Fibroblast growth factor 23 (FGF23) predicts progression of chronic kidney disease: themild to moderate kidney disease (MMKD) study," *J. Am. Soc. Nephrol.*, 18: 2601-2608, 2007.
Guebre-Egziabher et al., "Adiponectin in chronic kidney disease is related more to metabolic disturbances than to decline in renal function," *Nephrol. Dial. Transplant*, 20: 129-134, 2005.
Gutierrez et al., "Fibroblast growth factor-23 mitigates hyperphosphatemia but accentuates calcitriol deficiency in chronic kidney disease," *J. Am. Soc. Nephrol.*, 16: 2205-2215, 2005.
Iwashima et al., "Adiponectin and renal funciton, and implication as a risk of cardiovascular disease," *Am. J. Cardiology*, 98: 1603-1608, 2006.
Koiwa et al., "Sevelamer hydrochloride and calcium bicarbonate reduce serum fibroblast growth factor 23 levels in dialysis patients," *Therapeutic Apheresis and Dialysis*, 9 (4): 336-339, 2005.
Larsson et al., "Circulating concentration of FGF-23 increases as renal funciton declines in patients with chronic kidney disease, but does not change in response to variation in phosphate intake in healthy volunteers," *Kidney International*, 64: 2272-2279, 2003.
Menon et al., "Adiponectin and mortality in patients with chronic kidney disease," *J. Am. Soc. Nephrol.*, 17: 2599-2606, 2006.
PCT, International Search Report issued in Int. App. No. PCT/EP2008/000420, mailed Jul. 1, 2008.
Shen et al., "Up-regulation of adiponectin, its isoforms and receptors in end-stage kidney disease," *Nephrol. Dial. Transplant*, 22: 171-178, 2007.
International Preliminary Report on Patentability, issued in Int. App. No. PCT/EP2008/000420, mailed Jul. 28, 2009.

\* cited by examiner

*Primary Examiner* — Jacob Cheu
(74) *Attorney, Agent, or Firm* — Fulbright & Jaworski L.L.P.

(57) ABSTRACT

The present invention relates to a method for the determination or prediction of the progression of chronic kidney disease in a subject suspected to suffer from chronic kidney disease, said method comprising the step of determining the expression levels of at least one marker selected from (a) FGF23; and (b) adiponectin in a biological sample. Furthermore, the present invention relates to a use of a specific detection molecule for FGF23 or use of a specific detection molecule for adiponectin for the preparation of a diagnostic composition for the detection of chronic kidney disease or the progression of chronic kidney diseases in a subject suspected to suffer from said disease. In particular, the present invention also provides for use of FGF23 and/or of adiponectin as an in vitro marker for the presence, absence or progression of a chronic kidney disease and kits comprising a specific detection molecule for FGF23 or a specific detection molecule for adiponectin for use in the method of the present invention.

27 Claims, 17 Drawing Sheets

FIG. 5A

Figure 1:
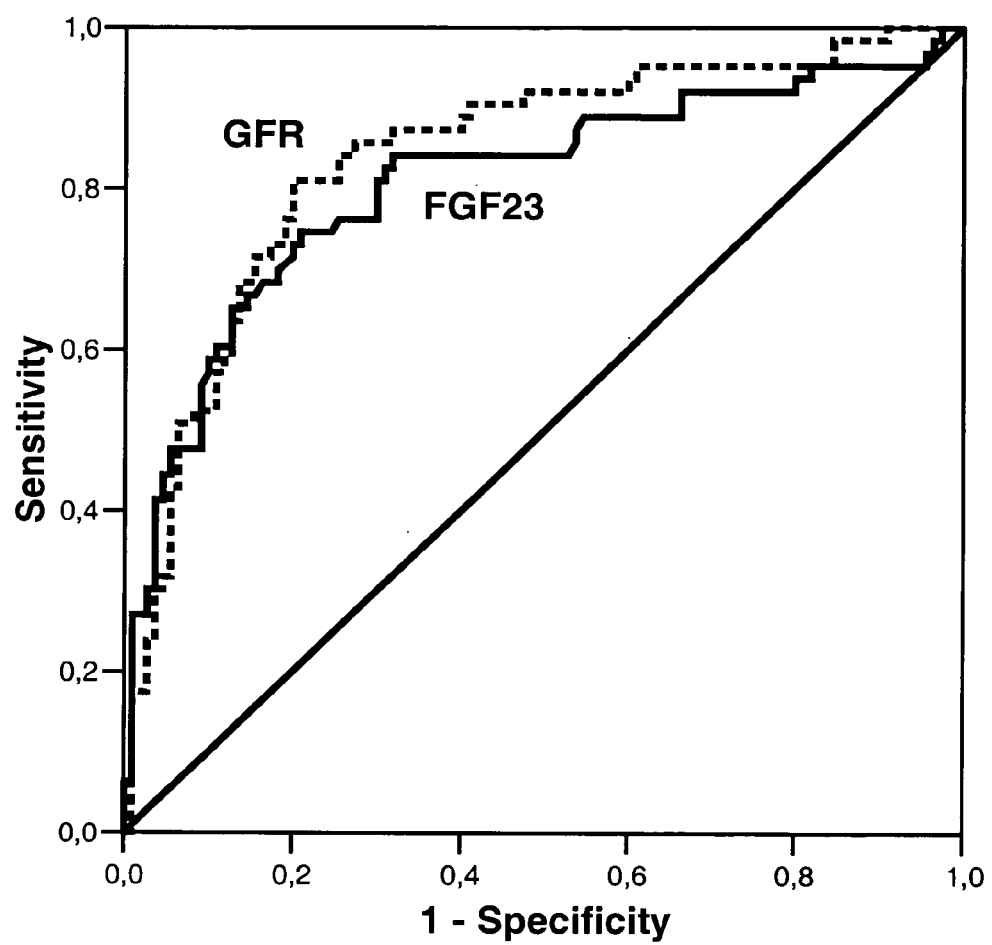

FGF23 (fibroblast growth factor 23)
(NCBI, dbSNP Build 126)

DESCRIPTION

The FGF23 gene encodes a member of the fibroblast growth factor family that is mutant in autosomal dominant hypophosphatemic rickets (ADHR; 193100).

Transcript Information

```
  1 CGGCAAAAAGGAGGGAATCCAGTCTAGGATCCTCACACCAGCTACTTGCAAGGGAGAAGG
    ............................................................
    ............................................................

61 AAAAGGCCAGTAAGGCCTGGGCCAGGAGAGTCCCGACAGGAGTGTCAGGTTTCAATCTCA
    ............................................................
    ............................................................

121 GCACCAGCCACTCAGAGCAGGGCACGATGTTGGGGCCCGCCTCAGGCTCTGGGTCTGTG
    ...........................ATGTTGGGGCCCGCCTCAGGCTCTGGGTCTGTG
    ...........................-M--L--G--A--R--L--R--L--W--V--C--

181 CCTTGTGCAGCGTCTGCAGCATGAGCGTCCTCAGAGCCTATCCCAATGCCTCCCCACTGC
 35 CCTTGTGCAGCGTCTGCAGCATGAGCGTCCTCAGAGCCTATCCCAATGCCTCCCCACTGC
 12 A--L--C--S--V--C--S--M--S--V--L--R--A--Y--P--N--A--S--P--L--

241 TCGGCTCCAGCTGGGGTGGCCTGATCCACCTGTACACAGCCACAGCCAGGAACAGCTACC
 95 TCGGCTCCAGCTGGGGTGGCCTGATCCACCTGTACACAGCCACAGCCAGGAACAGCTACC
 32 L--G--S--S--W--G--G--L--I--H--L--Y--T--A--T--A--R--N--S--Y--

301 ACCTGCAGATCCACAAGAATGGCCATGTGGATGGCGCACCCCATCAGACCATCTACAGTG
155 ACCTGCAGATCCACAAGAATGGCCATGTGGATGGCGCACCCCATCAGACCATCTACAGTG
 52 H--L--Q--I--H--K--N--G--H--V--D--G--A--P--H--Q--T--I--Y--S--

361 CCCTGATGATCAGATCAGAGGATGCTGGCTTTGTGGTGATTACAGGTGTGATGAGCAGAA
215 CCCTGATGATCAGATCAGAGGATGCTGGCTTTGTGGTGATTACAGGTGTGATGAGCAGAA
 72 A--L--M--I--R--S--E--D--A--G--F--V--V--I--T--G--V--M--S--R--
                                                              Y
421 GATACCTCTGCATGGATTTCAGAGGCAACATTTTTGGATCACACTATTTCGACCCGGAGA
275 GATACCTCTGCATGGATTTCAGAGGCAACATTTTTGGATCACACTATTTCGACCCGGAGA
 92 R--Y--L--C--M--D--F--R--G--N--I--F--G--S--H--Y--F--D--P--E--

481 ACTGCAGGTTCCAACACCAGACGCTGGAAAACGGGTACGACGTCTACCACTCTCCTCAGT
335 ACTGCAGGTTCCAACACCAGACGCTGGAAAACGGGTACGACGTCTACCACTCTCCTCAGT
112 N--C--R--F--Q--H--Q--T--L--E--N--G--Y--D--V--Y--H--S--P--Q--
                                        K         S
541 ATCACTTCCTGGTCAGTCTGGGCCGGGCGAAGAGAGCCTTCCTGCCAGGCATGAACCCAC
395 ATCACTTCCTGGTCAGTCTGGGCCGGGCGAAGAGAGCCTTCCTGCCAGGCATGAACCCAC
132 Y--H--F--L--V--S--L--G--R--A--K--R--A--F--=L--P--G--M--N--P--
```

FIG. 5B

```
 601 CCCCGTACTCCCAGTTCCTGTCCCGGAGGAACGAGATCCCCCTAATTCACTTCAACACCC
 455 CCCCGTACTCCCAGTTCCTGTCCCGGAGGAACGAGATCCCCCTAATTCACTTCAACACCC
 152 P--P--Y--S--Q--F--L--S--R--R--N--E--I--P--L--I--H--F--N--T--

R        Y
 661 CCATACCACGGCGGCACACCCGGAGCGCCGAGGACGACTCGGAGCGGGACCCCCTGAACG
 515 CCATACCACGGCGGCACACCCGGAGCGCCGAGGACGACTCGGAGCGGGACCCCCTGAACG
 172 P--I--P--=R--R--H--T--=R--S--A--E--D--D--S--E--R--D--P--L--N--

Y
 721 TGCTGAAGCCCCGGGCCCGGATGACCCCGGCCCCGGCCTCCTGTTCACAGGAGCTCCCGA
 575 TGCTGAAGCCCCGGGCCCGGATGACCCCGGCCCCGGCCTCCTGTTCACAGGAGCTCCCGA
 192 V--L--K--=P--R--A--R--M--T--P--A--P--A--S--C--S--Q--E--L--P--

781 GCGCCGAGGACAACAGCCCGATGGCCAGTGACCCATTAGGGGTGGTCAGGGGCGGTCGAG
 635 GCGCCGAGGACAACAGCCCGATGGCCAGTGACCCATTAGGGGTGGTCAGGGGCGGTCGAG
 212 S--A--E--D--N--S--P--M--A--S--D--P--L--G--V--V--R--G--G--R--

Y
 841 TGAACACGCACGCTGGGGGAACGGGCCCGGAAGGCTGCCGCCCCTTCGCCAAGTTCATCT
 695 TGAACACGCACGCTGGGGGAACGGGCCCGGAAGGCTGCCGCCCCTTCGCCAAGTTCATCT
 232 V--N--T--H--A--G--G--=T--G--P--E--G--C--R--P--F--A--K--F--I--

K
 901 AGGGTCGCTGGAAGGGCACCCTCTTTAACCCATCCCTCAGCAAACGCAGCTCTTCCCAAG
 755 AG..........................................................
 252 *-..........................................................

961 GACCAGGTCCCTTGACGTTCCGAGGATGGGAAAGGTGACAGGGGCATGTATGGAATTTGC
     ............................................................
     ............................................................

1021 TGCTTCTCTGGGGTCCCTTCCACAGGAGGTCCTGTGAGAACCAACCTTTGAGGCCCAAGT
     ............................................................
     ............................................................

1081 CATGGGGTTTCACCGCCTTCCTCACTCCATATAGAACACCTTTCCCAATAGGAAACCCCA
     ............................................................
     ............................................................

1141 ACAGGTAAACTAGAAATTTCCCCTTCATGAAGGTAGAGAGAAGGGGTCTCTCCCAACATA
     ............................................................
     ............................................................

1201 TTTCTCTTCCTTGTGCCTCTCCTCTTTATCACTTTTAAGCATAAAAAAAAAAAAAAAAAA
     ............................................................
     ............................................................

R
1261 AAAAAAAAAAAAAAAGCAGTGGGTTCCTGAGCTCAAGACTTTGAAGGTGTAGGGAAGAGGA
     ............................................................
     ............................................................

1321 AATCGGAGATCCCAGAAGCTTCTCCACTGCCCTATGCATTTATGTTAGATGCCCCGATCC
```

FIG. 5C

```
                                                          R
1381 CACTGGCATTTGAGTGTGCAAACCTTGACATTAACAGCTGAATGGGGCAAGTTGATGAAA

1441 ACACTACTTTCAAGCCTTCGTTCTTCCTTGAGCATCTCTGGGGAAGAGCTGTCAAAAGAC

1501 TGGTGGTAGGCTGGTGAAAACTTGACAGCTAGACTTGATGCTTGCTGAAATGAGGCAGGA

1561 ATCATAATAGAAAACTCAGCCTCCCTACAGGGTGAGCACCTTCTGTCTCGCTGTCTCCCT

1621 CTGTGCAGCCACAGCCAGAGGGCCCAGAATGGCCCCACTCTGTTCCCAAGCAGTTCATGA

1681 TACAGCCTCACCTTTTGGCCCCATCTCTGGTTTTTGAAAATTTGGTCTAAGGAATAAATA

1741 GCTTTTACACTGGCTCACGAAAATCTGCCCTGCTAGAATTTGCTTTTCAAAATGGAAATA

1801 AATTCCAACTCTCCTAAGAGGCATTTAATTAAGGCTCTACTTCCAGGTTGAGTAGGAATC

1861 CATTCTGAACAAACTACAAAAATGTGACTGGGAAGGGGGCTTTGAGAGACTGGGACTGCT

Y
1921 CTGGGTTAGGTTTTCTGTGGACTGAAAAATGGTGTCCTTTTCTCTAAATGAAGTGGCATC

R
1961 AAGGACTCAGGGGGAAAGAAATCAGGGGACATGTTATAGAAGTTATGAAAAGACAACCAC

2041 ATGGTCAGGCTCTTGTCTGTGGTCTCTAGGGCTCTGCAGCAGCAGTGGCTCTTCGATTAG
```

FIG. 5D

```
2101 TTAAAACTCTCCTAGGCTGACACATCTGGGTCTCAATCCCCTTGGAAATTCTTGGTGCAT
     ............................................................
     ............................................................

2161 TAAATGAAGCCTTACCCCATTACTGCGGTTCTTCCTGTAAGGGGGCTCCATTTTCCTCCC
     ............................................................
     ............................................................

2221 TCTCTTTAAATGACCACCTAAAGGACAGTATATTAACAAGCAAAGTCGATTCAACAACAG
     ............................................................
     ............................................................
                                                           W
2281 CTTCTTCCCAGTCACTTTTTTTTTCTCACTGCCATCACATACTAACCTTTTACTTTGAT
     ............................................................
     ............................................................

2341 CTATTCTTTTTGGTTATGAGAGAAATGTTGGGCAACTGTTTTTACCTGATGGTTTTAAGC
     ............................................................
     ............................................................
                                       R
2401 TGAACTTGAAGGACTGGTTCCTATTCTGAAACAGTAAAACTATGTATAATAGTATATAGC
     ............................................................
     ............................................................

2461 CATGCATGGCAAATATTTTAATATTTCTGTTTTCATTTCCTGTTGGAAATATTATCCTGC
     ............................................................
     ............................................................

2521 ATAATAGCTATTGGAGGCTCCTCAGTGAAAGATCCCAAAAGGATTTTGGTGGAAAACTAG
     ............................................................
     ............................................................

2581 TTGTAATCTCACAAACTCAACACTACCATCAGGGGTTTTCTTTATGGCAAAGCCAAAATA
     ............................................................
     ............................................................
                                           R
2641 GCTCCTACAATTTCTTATATCCCTCGTCATGTGGCAGTATTTATTTATTTATTTGGAAGT
     ............................................................
     ............................................................
         Y
2701 TTGCTTATCCTTCTATATTTATAGATATTTATAAAAATGTAACCCCTTTTTCCTTTCTTC
     ............................................................
     ............................................................

2761 TGTTTAAAATAAAAATAAAATTTATCTCAGCTTCTGTTAGCTTATCCTCTTTGTAGTACT
     ............................................................
     ............................................................

2821 ACTTAAAAGCATGTCGGAATATAAGAATAAAAAGGATTATGGGAGGGGAACATTAGGGAA
     ............................................................
```

FIG. 5E

2881 ATCCAGAGAAGGCAAAATTGAAAAAAAGATTTTAGAATTTTAAAATTTTCAAAGATTTCT

2941 TCCATTCATAAGGAGACTCAATGATTTTAATTGATCTAGACAGAATTATTTAAGTTTTAT

3001 CAATATTGGATTTCTGGT

FIG. 6A

Adiponectin

+605441 ADIPOCYTE, C1Q, AND COLLAGEN DOMAIN CONTAINING; ADIPOQ

*Alternative titles; symbols*

ADIPOSE MOST ABUNDANT GENE TRANSCRIPT 1; APM1 GELATIN-BINDING PROTEIN, 28-KD; GBP28 ADIPONECTIN ACRP30 ADIPOCYTE-SPECIFIC SECRETORY PROTEIN ACDC ADIPONECTIN DEFICIENCY, INCLUDED
Gene map locus 3q27

TEXT

DESCRIPTION

Adiponectin is a hormone secreted by adipocytes that regulates energy homeostasis and glucose and lipid metabolism. Adipocytes also produce and secrete proteins such as leptin (LEP: 164160), adipsin (factor D; 134350), various other complement components (e.g., properdin (see 138470) and C3a (see 120700)), and tumor necrosis factor (TNF; 191160), suggesting a possible link to the immune system. Adiponectin, an adipose tissue-specific plasma protein, has antiinflammatory effects on the cellular components of the vascular wall (13,14:Ouchi et al., 1999, 2000).

FIG. 6B

Transcript information

```
  1 AGGCTGTTGAGGCTGGGCCATCTCCTCCTCACTTCCATTCTGACTGCAGTCTGTGGTTCT
    ............................................................
    ............................................................

61 GATTCCATACCAGAGGGGCTCAGGATGCTGTTGCTGGGAGCTGTTCTACTGCTATTAGCT
    .........................ATGCTGTTGCTGGGAGCTGTTCTACTGCTATTAGCT
    .........................-M--L--L--L--G--A--V--L--L--L--L--A-

K
121 CTGCCCGGTCATGACCAGGAAACCACGACTCAAGGGCCCGGAGTCCTGCTTCCCCTGCCC
 37 CTGCCCGGTCATGACCAGGAAACCACGACTCAAGGGCCCGGAGTCCTGCTTCCCCTGCCC
 13 -L--P--G--H--D--Q--E--T--T--Q--G--P--G--V--L--P--L--P-

181 AAGGGGGCCTGCACAGGTTGGATGGCGGGCATCCCAGGGCATCCGGGCCATAATGGGGCC
 97 AAGGGGGCCTGCACAGGTTGGATGGCGGGCATCCCAGGGCATCCGGGCCATAATGGGGCC
 33 -K--G--A--C--T--G--W--M--A--G--I--P--G--H--P--G--H--N--G--A-

K
241 CCAGGCCGTGATGGCAGAGATGGCACCCCTGGTGAGAAGGGTGAGAAAGGAGATCCAGGT
157 CCAGGCCGTGATGGCAGAGATGGCACCCCTGGTGAGAAGGGTGAGAAAGGAGATCCAGGT
 53 -P-=G=-R--D--G--R--D--G--T--P--G--E--K--G--E--K--G--D--P--G-

301 CTTATTGGTCCTAAGGGAGACATCGGTGAAACCGGAGTACCCGGGGCTGAAGGTCCCCGA
217 CTTATTGGTCCTAAGGGAGACATCGGTGAAACCGGAGTACCCGGGGCTGAAGGTCCCCGA
 73 -L--I--G--P--K--G--D--I--G--E--T--G--V--P--G--A--E--G--P--R-

Y
361 GGCTTTCCGGGAATCCAAGGCAGGAAAGGAGAACCTGGAGAAGGTGCCTATGTATACCGC
277 GGCTTTCCGGGAATCCAAGGCAGGAAAGGAGAACCTGGAGAAGGTGCCTATGTATACCGC
 93 -G--F--P--G--I--Q--G--R--K--G--E--P--G--E--G--A--Y--V-=Y=-R-

421 TCAGCATTCAGTGTGGGATTGGAGACTTACGTTACTATCCCCAACATGCCCATTCGCTTT
337 TCAGCATTCAGTGTGGGATTGGAGACTTACGTTACTATCCCCAACATGCCCATTCGCTTT
113 -S--A--F--S--V--G--L--E--T--Y--V--T--I--P--N--M--P--I--R--F-

481 ACCAAGATCTTCTACAATCAGCAAAACCACTATGATGGCTCCACTGGTAAATTCCACTGC
397 ACCAAGATCTTCTACAATCAGCAAAACCACTATGATGGCTCCACTGGTAAATTCCACTGC
133 -T--K--I--F--Y--N--Q--Q--N--H--Y--D--G--S--T--G--K--F--H--C-

541 AACATTCCTGGGCTGTACTACTTTGCCTACCACATCACAGTCTATATGAAGGATGTGAAG
457 AACATTCCTGGGCTGTACTACTTTGCCTACCACATCACAGTCTATATGAAGGATGTGAAG
153 -N--I--P--G--L--Y--Y--F--A--Y--H--I--T--V--Y--M--K--D--V--K-

601 GTCAGCCTCTTCAAGAAGGACAAGGCTATGCTCTTCACCTATGATCAGTACCAGGAAAAT
517 GTCAGCCTCTTCAAGAAGGACAAGGCTATGCTCTTCACCTATGATCAGTACCAGGAAAAT
173 -V--S--L--F--K--K--D--K--A--M--L--F--T--Y--D--Q--Y--Q--E--N-

661 AATGTGGACCAGGCCTCCGGCTCTGTGCTCCTGCATCTGGAGGTGGGCGACCAAGTCTGG
577 AATGTGGACCAGGCCTCCGGCTCTGTGCTCCTGCATCTGGAGGTGGGCGACCAAGTCTGG
193 -N--V--D--Q--A--S--G--S--V--L--L--H--L--E--V--G--D--Q--V--W-
```

FIG. 6C

```
 721 CTCCAGGTGTATGGGGAAGGAGAGCGTAATGGACTCTATGCTGATAATGACAATGACTCC
 637 CTCCAGGTGTATGGGGAAGGAGAGCGTAATGGACTCTATGCTGATAATGACAATGACTCC
 213 -L--Q--V--Y--G--E--G--E--R--N--G--L--Y--A--D--N--D--N--D--S-

781 ACCTTCACAGGCTTTCTTCTCTACCATGACACCAACTGATCACCACTAACTCAGAGCCTC
 697 ACCTTCACAGGCTTTCTTCTCTACCATGACACCAACTGA.....................
 233 -T--F--T--G--F--L--L--Y--H--D--T--N--*-.....................

Y
 841 CTCCAGGCCAAACAGCCCCAAAGTCAATTAAAGGCTTTCAGTAC̲GGTTAGGAAGTTGATT
     ............................................................
     ............................................................

901 ATTATTTAGTTGGAGGCCTTTAGATATTATTCATTCATTTACTCATTCATTTATTCATTC
     ............................................................
     ............................................................

R                                      M
 961 ATTCATCG̲AGTAACTTTAAAAAAATCATATGCTATGTTCCCAGTCG̲TGGGGAGCTTCACA
     ............................................................
     ............................................................

1021 AACATGACCAGATAACTGACTAGAAAGAAGTAGTTGACAGTGCTATTTTGTGCCCACTGT
     ............................................................
     ............................................................

1081 CTCTCCTGATGCTCATATCAATCCTATAAGGCACAGGGAACAAGCATTCTCCTGTTTTTA
     ............................................................
     ............................................................

1141 CAGATTGTATCCTGAGGCTGAGAGAGTTAAGTGAATGTCTAAGGTCACACAGTATTAAGT
     ............................................................
     ............................................................

K
1201 GACAGTGCTAGAAATCAAACCCAGAGCTGTGGACTTTGTTCACTAGACTGTG̲CCCTTTTA
     ............................................................
     ............................................................

1261 TAGAGGTACATGTTCTCTTTGGAGTGTTGGTAGGTGTCTGTTTCCCACCTCACCTGAGAG
     ............................................................
     ............................................................

1321 CCATTGAATTTGCCTTCCTCATGAATTAAAACCTCCCCCAAGCAGAGCTTCCTCAGAGAA
     ............................................................
     ............................................................

M
1381 AGTGGTTCTATGATGAG̲GTCCTGTCTTGGAAGGACTACTACTCAATGGCCCCTGCACTAC
     ............................................................
     ............................................................

1441 TCTACTTCCTCTTACCTATGTCCCTTCTCATGCCTTTCCCTCCAACGGGGAAAGCCAACT
     ............................................................
     ............................................................
```

FIG. 6D

```
                   Y
1501 CCATCTCTAAGTGCGGAACTCATCCCTGTTCCTCAAGGCCACCTGGCCAGGAGCTTCTCT
     ............................................................
     ............................................................

1561 GATGTGATATCCACTTTTTTTTTTTTGAGATGGAGTCTCACTCTGTCACCCAGGCTGGA
     ............................................................
     ............................................................

1621 GTACAGTGACACGACCTCGGCTCACTGCAGCCTCCTTCTCCTGGGTCCAAGCAATTATTG
     ............................................................
     ............................................................

1681 TGCCTCAGCCTCCCGAGTAGCTGAGACTTCAGGTGCATTCCACCACACATGGCTAATTTT
     ............................................................
     ............................................................

R
1741 TGTATTTTTAGTAGAAATGGGGTTTCGTCATGTTGGCCAGGCTGGTCTCGAACTCCTGGC
     ............................................................
     ............................................................

R
1801 CTAGGTGATCCACCCGCCTCGACCTCCCAAAGTGCTGGGATTACAGGCATGAGCCACCAT
     ............................................................
     ............................................................

1861 GCCCAGTCGATATCTCACTTTTTATTTTGCCATGGATGAGAGTCCTGGGTGTGAGGAACA
     ............................................................
     ............................................................

1921 CCTCCCACCAGGCTAGAGGCAACTGCCCAGGAAGGACTGTGCTTCCGTCACCTCTAAATC
     ............................................................
     ............................................................

R
1981 CCTTGCAGATCCTTGATAAATGCCTCATGAAGACCAATCTCTTGAATCCCATATCTACCC
     ............................................................
     ............................................................

2041 AGAATTAACTCCATTCCAGTCTCTGCATGTAATCAGTTTTATCCACAGAAACATTTTCAT
     ............................................................
     ............................................................

2101 TTTAGGAAATCCCTGGTTTTAAGTATCAATCCTTGTTCAGCTGGACAATATGAATCTTTT
     ............................................................
     ............................................................

2161 CCACTGAAGTTAGGGATGACTGTGATTTTCAGAACACGTCCAGAATTTTTCATCAAGAAG
     ............................................................
     ............................................................

2221 GTAGCTTGAGCCTGAAATGCAAAACCCATGGAGGAATTCTGAAGCCATTGTCTCCTTGAG
```

FIG. 6E

```
2281 TACCAACAGGGTCAGGGAAGACTGGGCCTCCTGAATTTATTATTGTTCTTTAAGAATTAC

2341 AGGTTGAGGTAGTTGATGGTGGTAAACATTCTCTCAGGAGACAATAACTCCAGTGATGTT

Y           K
2401 GTTCAAAGATTTTAGCAAAAACAGAGTAAATAGCATTCTCTATCAATATATAAATTTAAA

Y                      Y
2461 AAACTATCTTTTTGCTTACAGTTTTAAATCCTGAACAATTCTCTCTTATATGTGTATTGC

2521 TAATCATTAAGGTATTATTTTTTCCACATATAAAGCTTTGTCTTTTTGTTGTTGTTGTTG

Y
2581 TTTTTAAGATGGAGTTTCCCTCTGTTGCCAGGCTAGAGTGCAGTGGCATGATCTCGGCTT

Y
2641 ACTGCAACCTTTGCCTCCCAGGTTCAAGCGATTCTTCTGCCTCAGCCTCCCGAGTAGCTG

2701 GGACCACAGGTGCCTACCACCATGCCAGGCTAATTTTTGTATTTTTAGTAAAGACAGGGT

R
2761 TTCACCATATTGGCCAGGCTGGTCTCGAACTCCTGACCTTGTGATCTGCCCGCCTCCATT

2821 TTTGTTGTTATTTTTTGAGAAAGATAGATATGAGGTTTAGAGAGGGATGAAGAGGTGAGA

2881 GTAAGCCTTGTGTTAGTCAGAACTCTGTGTTGTGAATGTCATTCACAACAGAAAACCCAA

2941 AATATTATGCAAACTACTGTAAGCAAGAAAAATAAAGGAAAAATGGAAACATTTATTCCT
```

FIG. 6F

```
3001 TTGCATAATAGAAATTACCAGAGTTGTTCTGTCTTTAGATAAGGTTTGAACCAAAGCTCA
     ............................................................
     ............................................................

3061 AAACAATCAAGACCCTTTTCTGTATGTCCTTCTGTTCTGCCTTCCGCAGTGTAGGCTTTA
     ............................................................
     ............................................................

3121 CCCTCAGGTGCTACACAGTATAGTTCTAGGGTTTCCCTCCCGATATCAAAAAGACTGTGG
     ............................................................
     ............................................................

3181 CCTGCCCAGCTCTCGTATCCCCAAGCCACACCATCTGGCTAAATGGACATCATGTTTTCT
     ............................................................
     ............................................................

3241 GGTGATGCCCAAAGAGGAGAGAGGAAGCTCTCTTTCCCAGATGCCCCAGCAAGTGTAACC
     ............................................................
     ............................................................

3301 TTGCATCTCATTGCTCTGGCTGAGTTGTGTGCCTGTTTCTGACCAATCACTGAGTCAGGA
     ............................................................
     ............................................................

3361 GGATGAAATATTCATATTGACTTAATTGCAGCTTAAGTTAGGGGTATGTAGAGGTATTTT
     ............................................................
     ............................................................

3421 CCCTAAAGCAAAATTGGGACACTGTTATCAGAAATAGGAGAGTGGATGATAGATGCAAAA
     ............................................................
     ............................................................

3481 TAATACCTGTCCACAACAAACTCTTAATGCTGTGTTTGAGCTTTCATGAGTTTCCCAGAG
     ............................................................
     ............................................................

3541 AGACATAGCTGGAAAATTCCTATTGATTTTCTCTAAAATTTCAACAAGTAGCTAAAGTCT
     ............................................................
     ............................................................

3601 GGCTATGCTCACAGTCTCACATCTGGTTGGGGTGGGCTCCTTACAGAACACGCTTTCACA
     ............................................................
     ............................................................
                                                              s
3661 GTTACCCTAAACTCTCTGGGGCAGGGTTATTCCTTTGTGGAACCAGAGGCACAGAGAGAG
     ............................................................
     ............................................................

3721 TCAACTGAGGCCAAAAGAGGCCTGAGAGAAACTGAGGTCAAGATTTCAGGATTAATGGTC
     ............................................................
```

FIG. 6G

```
                                      W
3781 CTGTGATGCTTTGAAGTACAATTGTGGATTTGTCCAATTCTCTTTAGTTCTGTCAGCTTT

3841 TGCTTCATATATTTTAGCGCTCTATTATTAGATATATACATGTTTAGTATTATGTCTTAT

3901 TGGTGCATTTACTCTCTTATCATTATGTAATGTCCTTCTTTATCTGTGATAATTTTCTGT

3961 GTTCTGAAGTCTACTTTGTCTAAAAATAACATACGCACTCAACTTCCTTTTCTTTCTTCC

4021 TTCCTTTCTTTCTTCCTTCCTTTCTTTCTCTCTCTCTCTCTTTCCTTCCTTCCTTCCTCC

4081 TTTTCTTTCTCTCTCTCTCTCTCTCTCTTTTTTTGACAGACTCTCGTTCTGTGGCCCTGG
                      Y
4141 CTGGAGTTCAGTGGTGTGATCTTGGCTCACTGCTACCTCTACCATGAGCAATTCTCCTGC

4201 CTCAGCCTCCCAAGTAGCTGGAACTACAGGCTCATGCCACTGCGCCCAGCTAATTTTTGT
                                                             Y

4261 ATTTTTCGTAGAGACGGGGTTTCACCACATTCGTCAGGTTGGTTTCAAACTCCTGACTTT
                                                    R
4321 GTGATCCACCCGCCTCGGCCTCCCAAAGTGCTGGATTACAGGCATGAGCCATCACACCT

4381 GGTCAACTTTCTTTTGATTAGTGTTTTTGTGGTATATCTTTTTCCATCATGTTACTTTAA

4441 ATATATCTATATTATTGTATTTAAAATGTGTTTCTTACAGACTGCATGTAGTTGGGTATA
```

FIG. 6H

```
4501 ATTTTTATCCAGTCTAAAAATATCTGTCTTTTAATTGGTGTTTAGACAATTTATATTTAA
     ............................................................
     ............................................................

4561 TAAAATTGTTGAATTT
     ................
     ................
```

MARKERS FOR CHRONIC KIDNEY DISEASE

The present application is a national phase application under 35 U.S.C. §371 of International Application No. PCT/EP2008/000420 filed Jan. 21, 2008, which claims priority to European Application No. 07001340.4 filed Jan. 22, 2007 the entire text and figures of which disclosures are incorporated herein by reference without disclaimer.

The present invention relates to a method for the determination or prediction of the progression of chronic kidney disease in a subject suspected to suffer from chronic kidney disease, said method comprising the step of determining the expression levels of at least one marker selected from (a) FGF23; and (b) adiponectin in a biological sample. Furthermore, the present invention relates to a use of a specific detection molecule for FGF23 or use of a specific detection molecule for adiponectin for the preparation of a diagnostic composition for the detection of chronic kidney disease or the progression of chronic kidney diseases in a subject suspected to suffer from said disease. In particular, the present invention also provides for use of FGF23 and/or of adiponectin as an in vitro marker for the progression of a chronic kidney disease and kits comprising a specific detection molecule for FGF23 or a specific detection molecule for adiponectin for use in the method of the present invention.

The kidney contains a vast amount of vessels of different size and function with an enormous endothelial surface. As a consequence, pathophysiological conditions involving the vascular bed are not only related to atherosclerotic changes of major vessels of the heart and the brain, but also to vascular changes within the kidney. It has been even proposed that glomerulosclerosis and atherosclerosis share common pathophysiological pathways (Kasiske, (1987) Kidney Int. 31, 1153-1159). However, little is known about the exact mechanisms (Diamond, (1992) Annu. Rev. Med. 43, 83-92), and factors related to atherosclerosis as well as glomerular-endothelial injury might be interesting candidates to be involved in the progression of kidney disease.

One of these putative candidates is adiponectin, the major adipocyte secretory protein. It has been demonstrated to improve insulin sensitivity and to possess anti-inflammatory and anti-atherosclerotic properties (Rabin, (2005) Expert Rev. Cardiovasc. Ther. 3, 465-471). Hypoadiponectinaemia has been found to be associated with insulin resistance (Weyer, (2001) J. Clin. Endocrinol. Metab. 86, 1930-1935; Zoccali, (2002) J. Am. Soc. Nephrol. 13, 134-141), obesity and other features of the metabolic syndrome (Menzaghi, (2002) Diabetes 51, 2306-2312; Kazumi, (2002) Diabetes Care 25, 971-9766; Gonzalez-Sanchez, (2005) Obes. Res. 13, 807-812) as well as type 2 diabetes mellitus and cardiovascular disease. Recent data suggested that the presence of the metabolic syndrome might be a causal factor for chronic kidney disease (CKD) (Chen, (2004) Ann. Intern. Med. 140, 167-174; Kurella, (2005) J. Am. Soc. Nephrol. 16, 2134-2140). In addition, it was shown, that insulin resistance is present already in patients with mild degrees of renal impairment and even in patients with primary CKD and normal glomerular filtration rate (GFR) (Becker, (2005) J. Am. Soc. Nephrol. 16, 1091-1098).

Disturbed calcium-phosphate metabolism affects cardiovascular morbidity and mortality in patients with chronic kidney disease (CKD), and particularly in patients with end-stage renal disease, (Block, (2004) J. Am. Soc. Nephrol. 15, 2208-2218; Schmitt, (2006) J. Am. Soc. Nephrol. 17 (Suppl. 2), S78-80). So far, it has not been firmly established whether it also contributes to CKD progression. Among factors related to calcium-phosphate metabolism in patients with CKD, potential culprits for progression are hyperphosphatemia, hyperparathyroidism, lack of active vitamin D, and possibly excess of the phosphaturic hormone fibroblast growth factor 23 (FGF23) (Ritz, (2005) Kidney Int. 68 (Suppl. 99), S66-S70). Early experimental work suggested a parathyroid hormone (PTH)-independent beneficial role of phosphate restriction on CKD progression in rats (Tomford, (1981) J. Clin. Invest. 68, 655-664), but it has to be pointed out that these animals have physiologic hyperphosphatemia. Furthermore, data from human studies on this issue are limited to uncontrolled observations. There is also little direct experimental or clinical evidence for a role of PTH in accelerating CKD progression (Ritz, (2005), loc. cit.), although results from recent experimental studies documented that CKD progression is significantly attenuated by administration of calcimimetics or by parathyroidectomy (Ogata, (2003) J. Am. Soc. Nephrol. 14, 959-967). However, the confounding effect of lower blood pressure values in these experimental settings cannot be excluded. The most solid evidence for an effect on CKD progression exists for active vitamin D ($1,25$-$OH_2D_3$). In the past, it was assumed that vitamin D therapy is "nephrotoxic", but this was probably the result of vitamin D-induced hypercalcemia in patients with CKD (Christiansen, (1978) Lancet 2, 700-703). In contrast, recent experimental evidence clearly revealed that $1,25$-$OH_2D_3$ and its analogues attenuate progression in various CKD models (Ritz, (2005), loc. cit; Schwarz, (1998) Kidney Int. 53, 1696-1705; Panichi, (2001), Kidney Int. 60, 87-95).

There is a need in the art for reliable markers or marker systems which allow a monitoring and/or evaluation of the starting of chronic kidney disease in particular in human patients suffering from said disorder or suspected to suffer from said disorder. The solution to said technical problem is provided in the embodiments provided herein and as characterized in the claims.

Accordingly, the present invention relates to a method for the determination or prediction of the progression of chronic kidney disease in a subject suspected to suffer from chronic kidney disease, said method comprising the step of determining the expression levels of at least one marker selected from
a) FGF23; and
b) adiponectin
in a biological sample.

As documented in the appended examples, it was surprisingly found in the context of the invention that the fibroblast growth factor 23 (FGF-23) and adiponectin are, independently (but also in combination), very predictive markers for the progression of chronic kidney disease (CKD). Accordingly, the two markers identified herein are very useful indicators of the progression of the disease, in particular in non-diabetic patients. Especially FGF23 is a particularly good and also independent predictor for progression of CKD, in particular in non-diabetic patients. It is of note that in particular in male human patients both markers (FGF23 and adiponectin) may be measured in order to determine the progression or potential progression of CKD. The values for the expression level or the corresponding quantitative values of FGF-23 and/or adiponectin are useful in the prediction of a progression, in particular also and specifically for fast progression of CKD. A "fast progression" is meant that the progression endpoint is reached significantly faster, e.g. at least 10% or at least 20% or at least 30% faster when compared to an average (clinical or disease) progression. As shown in the appended example two a "fast progression" to the (renal) progression endpoint was reached in about 40 to 50 month (average 46.9 month), whereas in slower progression said endpoint was reached in about 65 to 80 month (average 72.5 month).

The present invention now provides for a needed diagnostic tool for practitioners (like, clinicians) in order to determine whether a progression of CKD is fast or slow or whether said CKD has the potential of a fast or slow progression. This is of particular importance since the clinical avenues to be taken in order to ameliorate the medical condition of a CKD patient (human as well as non-human patients) depends on the prediction how the disease will develop/progress; see also experimental part of this invention and further description herein below The gist of the present invention can, inter alia, be seen in the provision of method for the determination of the (potential) progression of CKD. Also the corresponding means and methods are provided herein. In short, the present invention provides for the teaching that a clear and strong correlation between the expression level of fibroblast growth factor 23/FGF23 (and/or of adiponectin) and the progression of chronic kidney disease (CKD) can be drawn. The determination of "expression levels" is, e.g., carried out by a comparison of the expression levels to be determined (in a given test sample) with (for example) corresponding standard controls or base line values. Standard controls/baseline values and the like are explained in detail herein below. Therefore, the present invention also provides for an in vitro method for the determination of the progression of CKD, said method comprising the step of determining the expression level of FGF23 and/or of adiponectin in a sample from a subject to be analyzed (test sample) and comparing said expression level of FGF23 and/or of adiponectin to baseline values (or normal standards or optimal cut-off rates or the like; control sample) and determining whether said test sample comprises a higher expression level of FGF23 and/or of adiponectin than the corresponding sample, whereby the elevated FGF23 and/or of adiponectin is indicative and correlated to the progression of the chronic kidney disease. The higher the expression level in the given test sample, the higher the likelihood for a fast progression of the disease. Accordingly, it was for example surprisingly found in the present invention that a higher FGF23 expression (compared to a normal standard or a FGF23-level above the optimal/normal cut-off or compared to baseline values) is clearly correlated with a faster progression of CKD. Similarly, it was found that elevated levels (as compared to a baseline value or a normal standard or the like) of adiponectin is indicative for the progression of CKD. Another important finding of the present invention is that the correlation of FGF23 expression level(s) and the progression of CKD appears to be independent form sex/gender, whereas adiponectin is a particular good marker for the progression of CKD in male subject, in particular human male subjects. It is also important to note that the correlation of FGF23 and adiponectin expression level(s) with the progression of CKD is independent from GFR.

As shown herein in the experimental part, evaluated patients with FGF23 blood levels above the optimal out-off level of about 100 rU/ml (considering and employing the ELISA-test system from Immutopics Inc, Cat. Number 60-6500, whereby 104 rU/ml were established) in serum had a significant faster progression and, accordingly, a specific, modified medical treatment regime may be necessary and is indicated. Since assays for FGF23 are not yet fully standardized the measurements of one assay are not necessarily identical to those from another assay. Therefore systematic differences are expected and the cut-offs proposed herein may be different from other assays. To extrapolate the proposed cut-off for other test systems one could determine the same e.g. 50 plasma or serum samples with the assay used herein in comparison to an assay which should be evaluated. The cut-off for this assay can be extrapolated by adjusting for the systematic differences between the two assays. If the assay used herein shows a mean value of e.g. 150 rU/ml and the other assay shows a mean value of 200 µg/mL, the optimal cutoff for the latter assay has to be increased by 30% compared to assay used herein and illustrated in the appended examples.

Similarly, in particular male human patients with adiponectin levels above their ROC (ROC is defined herein below) analysis-derived optimal out-off at least 3 µg/ml (as shown in the appended examples 4 µg/ml in a particular test system) had a significant faster progression of CKD and need, accordingly, specified and modified medical attention.

Although the described method for the determination or prediction of the progression of chronic kidney disease preferably is performed on a human subject, it is evident for the skilled artisan that the method of the present invention may also be useful for the determination or prediction of the progression of chronic kidney disease of other animal species than humans. The method of the present invention is also useful for determining or predicting the progression of chronic kidney disease of domesticated animals including, but not limited to, dogs (*Canis lupus familiaris*) cats (*Felis silvestris catus*) and horses (*Equus caballus*). Particularly preferred are male dogs, cats and horses, e.g. stallions. Again, as described herein for human patients or human subject the methods of the determination of "elevated levels" or "elevated expression levels" of FGF23 and/or adiponectin applies here mutatis mutandis. As for human subjects, there is a clear correlation between the expression level of FGF23 (and/or adiponectin) and the progression of CKD. The higher the expression level of FGF23 (and/or adiponectin) the faster CKD progresses.

Since assays for adiponectin are not yet fully standardized the measurements of one assay are not necessarily identical to those from another assay to be employed. Therefore systematic differences are expected and the cut-offs proposed herein may be different from other assays. To extrapolate the proposed cut-off for other test systems one could determine/evaluate the same e.g. 50 plasma or serum samples with the assay used herein well as with the assay which should be evaluated. The cutoff for this assay can be extrapolated by adjusting for the systematic differences between the two assays. If the assay used by us shows a mean value of e.g. 6 µg/mL and the other assay shows a mean value of 9 µg/mL, the optimal cutoff for the latter assay has to be increased by 50% compared to the assay employed herein and provided in the appended examples.

It is of note that predictive numerical values given herein are relative values since elevated levels may also be determined by other test systems/assay systems used in the experimental part. That means that the values given herein above (i.e. at least 100 rU/ml as far as FGF23 is concerned and at least 3 µg/ml as far as adiponectin is concerned) are related to the specific assay used. However, the person skilled in the art is readily in a position to adopt any other test system to the techniques provided herein. Accordingly, the inventive teaching of the present invention is the fact that elevated levels (as compared to a baseline value) of FGF23 and/or adiponectin is indicative for the progression of CKD.

As shown with the specific test systems employed in the experimental part, in 177 patients evaluated, a blood (serum or plasma) level of more than 100 rU/ml (specifically 104 rU/ml) of FGF23 and an adiponectin level above the optimal cut-off of more than 3 µg/ml (e.g. 4 µg/ml) is indicative for a faster progression of CKD. The values provide herein are non-limiting values for human subjects Again, it is of note values provided herein are illustrative and the skilled artisan is aware of the fact that such values are assay/test dependant. The experimental part provided herein below gives the person skilled in the art a guidance how expression levels of the marker(s) for the progression of CKD can be measured and how given "elevated" or given "normal" expression levels can be deduced in any given sample from the (human and non-human) subject to be analyzed. One tool for this assessment is the Receiver Operating Characteristics (ROC) curve.

The Receiver Operating Characteristics (ROC) curve as used herein derives its name from its first application—measuring the ability of radar operators to distinguish radar signals from noise. For the purposes of diagnostic testing, a graph is constructed with sensitivity (sometimes labeled as the true-positive rate) on the vertical axis, and 1−specificity (sometimes labeled as the false-positive rate) on the horizontal axis. At each cutoff point, sensitivity and 1−specificity will be calculated. These results then can be graphed along the full range of cutoff points, producing the ROC curve (Definition from. Greenberg et al. "Medical Epidemiology", Lange Medical Books/McGraw-Hill, Medical Publishing Division, fourth edition, 2005). Furthermore, the Receiver Operating Characteristics (ROC) analysis-derived optimal cutoff is calculated as follows. A newly arranged dataset comprises the following variables: the laboratory parameter "xxx" (any given laboratory parameter), the variable sensitivity, and the variable 1−specificity derived from ROC analysis. One has to first calculate 1 minus (1−specificity). As a next step, this calculated variable, called specificity, and the variable sensitivity are summed up, further, this variable, called cutoff, is sorted in ascending order, and the highest value of this variable is taken as the optimal cutoff for the given laboratory parameter "xxx". Definitions for "sensitivity" and "specificity" are known in the art in this context, see, inter alia, Brenner and Rector "The Kidney" (2004), Saunders Pub. Philadelphia Chapter 24. The above recited method for the determination of optimal cut-offs is also laid down in Lin (2002), Int. J. Obesity 26, 1232-1238.

In context of the present invention the term "progression of chronic kidney disease" or "chronic kidney disease progression" means, for example, a doubling of baseline serum (or plasma) creatinine concentration and/or terminal real failure necessitating renal replacement therapy, like dialysis (hemodialysis, peritoneal dialysis) or even renal transplantation. The definition of the "progression of chronic kidney disease" is very well known in the art and is, inter alia illustrated in Brenner and Rector "The Kidney", (2004) Saunders pub. Philadelphia. Accordingly, the "progression of chronic kidney disease" can be determined, in a primary endpoint, as the doubling of the base-line serum creatinine or the need for dialysis or kidney transplantation; see also Maschio (1996) N. Engl. J. Med 334, 939-945.

"Determining the expression levels" of any one of the two markers defined herein means of the treatment that the protein concentration, in particular in blood serum and/or blood plasma is to be determined, i.e. as a function of protein expression and/or presence of the protein in the corresponding biological samples, like blood, serum or plasma.

In a particular preferred embodiment of the invention, the claimed method comprises the determination of the expression level of said adiponectin in biological samples from male subjects (in particular human male subjects/patients) suspected to suffer from chronic kidney disease, in particular the herein defined marker adiponectin is a surprisingly strong predictive marker for the progression of CKD in male patients, in particular human male patients.

The subject suspected to suffer from chronic kidney disease may show renal impairment or dysfunction (e.g. elevated creatinine levels, decrease of GFR, and the like), or from primary kidney disease. Yet, it is of note that the present invention and the methods provided herein are also envisaged to be useful in other forms of chronic kidney disease, like diabetic nephropathy. However, the focus of this invention is in the experimental part laid on non-diabetic kidney impairments.

One example of a primary kidney disease is a non-diabetic kidney disease, however also in diabetic patients the progression of CKD may be measured, analyzed and/or evaluated by the use of the means and methods provided herein.

The methods provided herein are in particular useful in the determination (i.e. measurement, analysis and/or evaluation) of the progression of a chronic kidney disease, like a primary kidney disease whereby said primary kidney disease may be selected from the group consisting of glomerulonephritis, adult polycystic kidney disease, and interstitial nephritis and various other types of kidney disease including even patients in whom the exact diagnosis is unknown.

A known diabetic kidney disease, the progression of which may be assessed by the methods provided here may be diabetic nephropathy.

In the method provided herein said expression level of said at least one marker selected from FGF23 and/or adiponectin is determined in a biological sample from a subject suspected to suffer from chronic kidney disease and said expression level is compared to a standard control or a reference sample. Such a standard control may be or can be derived from a biological sample of a healthy control individual or from healthy control individuals of the same species as the subject suspected to suffer from a chronic kidney disease. It is also possible that such a standard control is or is derived from an earlier sample from the patient to be diagnosed, i.e. an older blood-, serum- or plasma-sample which was obtained before the onset of CKD.

In a particular preferred embodiment of the invention, said determination of the expression levels of at least one marker selected from FGF23 and/or adiponectin comprises the detection of the FGF23 protein and/or the adiponectin protein in said biological sample or said biological samples. This is also illustrated in the appended examples.

The person skilled in the art is fully aware that the term FGF23 in context of this invention is the fibroblast growth factor 23. The FGF23 gene encodes a member of the fibroblast growth factor family that is mutant in autosomal dominant hydrophosphatemic rickets (ADHR; 193100). In the enclosed sequence listing as provided herewith, the FGF23 coding nucleic acid sequence as well as the corresponding amino acid sequence of human FGF23 (SEQ ID NO: 1 for the nucleic acid sequence and SEQ ID NO: 2 for the amino acid sequence), cat FGF23 (SEQ ID NO: 3 for the nucleic acid sequence and SEQ ID NO: 4 for the amino acid sequence) and dog FGF23 (SEQ ID NO: 5 for the nucleic acid sequence and SEQ ID NO: 6 for the amino acid sequence) is provided. Human FGF23 sequences can also be obtained under NM_020638 or NP_065689 in NCBI Build 35.1 Ensembl. A corresponding reference sequence of human FGF23 is also provided in the appended FIG. 5 (nucleic acid molecule and amino acid sequence).

The coding nucleic acid sequence and/or the corresponding amino acid sequence of FGF23 of other animal species than the herein provided sequences for human-, cat- and dog FGF23 can be identified by the skilled person using methods known in the art, e.g. by using hybridization assays or by using alignments, either manually or by using computer programs such as those mentioned herein below in connection with the definition of the term "hybridization" and degrees of homology. In one embodiment, the nucleic acid sequence encoding for orthologs of human FGF23 is at least 70%, at least 75%, at least 78%, at least 80%, more preferably at least 90% homologous to the nucleic acid sequence as shown in SEQ ID NO. 1 or the amino acid sequence as shown in SEQ ID NO. 2 or the nucleic acid or amino acid sequences shown in FIG. 5.

Also adiponectin is very well known in the art and is an adipokine with potent anti-inflammatory and anti-atherosclerotic properties. In the enclosed sequence listing the corresponding coding sequences and corresponding amino acid sequences of human adiponectin (SEQ ID NO: 7 for the nucleic acid sequence and SEQ ID NO: 8 for the amino acid sequence), cat adiponectin (SEQ ID NO: 9 for the nucleic acid sequence and SEQ ID NO: 10 for the amino acid sequence) and dog adiponectin (SEQ ID NO: 11 for the nucleic acid sequence and SEQ ID NO: 12 for the amino acid sequence) are provided. Human adiponectin sequences can also be obtained NM_004797, NP_004788.1 on the NCBI database (build 35.1 Ensembl). In addition thereto, a corresponding reference sequence of human adiponectin is also provided in the appended FIG. 6 (nucleic acid molecule and amino acid sequence).

The coding nucleic acid sequence and/or the corresponding amino acid sequence of adiponectin of other animal species than the herein provided sequences for human-, cat- and dog adiponectin can be identified by the skilled person using methods known in the art, e.g. by using hybridization assays or by using alignments, either manually or by using computer programs such as those mentioned herein below in connection with the definition of the term "hybridization" and degrees of homology. In one embodiment, the nucleic acid sequence encoding for orthologs of human adiponectin is at least 75%, at least 80%, at least 83%, at least 85%, more preferably at least 90% homologous to the nucleic acid sequence as shown in SEQ ID NO. 7 or the amino acid sequence as shown in SEQ ID NO. 8. or the nucleic acid or amino acid sequences as shown in FIG. 6.

Hybridization assays for the characterization of orthologs of known genes/proteins are well known in the art; see e.g. Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989). The term "hybridization" or "hybridizes" as used herein may relate to hybridizations under stringent or non-stringent conditions. If not further specified, the conditions are preferably non-stringent. Said hybridization conditions may be established according to conventional protocols described, e.g., in Sambrook (2001) loc. cit.; Ausubel (1989) loc. cit., or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions.

In accordance with the present invention, the terms "homology" or "percent homology" or "identical" or "percent identity" in the context of two or more nucleic acid or amino acid sequences refers to two or more sequences or subsequences that are the same, or that have a specified percentage of amino acid residues or nucleotides that are the same (e.g. 75% identity, preferably, 80% identity, more preferably 83-85% identity, most preferably at least 90% identity), when compared and aligned for maximum correspondence over a window of comparison, or over a designated region as measured using a sequence comparison algorithm as known in the art, or by manual alignment and visual inspection. Sequences having, for example, 75% to 90% or greater sequence identity may be considered to be substantially identical. Such a definition also applies to the complement of a test sequence. Preferably the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215: 403-410). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff (1989) PNAS 89:10915) uses alignments (B) of 50, expectation (E) of 10, M=5, N=4, and a comparison of both strands.

In order to determine whether an amino acid residue or nucleotide residue in a nucleic acid sequence corresponds to a certain position in the amino acid sequence or nucleotide sequence of e.g. SEQ ID NOs:1, 2, 7 or 8, the skilled person can use means and methods well-known in the art, e.g., alignments, either manually or by using computer programs such as those mentioned herein. For example, BLAST 2.0, which stands for Basic Local Alignment Search Tool BLAST (Altschul (1997), loc. cit.; Altschul (1993), loc. cit.; Altschul (1990), loc. cit.), can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cut-off score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum } BLAST \text{ score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules. Another example for a program capable of generating sequence alignments is the CLUSTALW computer program (Thompson (1994) Nucl. Acids Res. 2:4673-4680) or FASTDB (Brutlag (1990) Comp. App. Biosci. 6:237-245), as known in the art.

It is evident for the skilled person that the test systems/assay systems used to determine the expression level of FGF23 and/or adiponectin are adapted to the animal species to be tested. For instance, a test system/assay system suitable for measuring human FGF23 or human adiponectin is used to measure FGF23 and/or adiponectin in human subjects.

The biological sample to be used and/or assayed in the method of the present invention may be a tissue sample, a cell sample or a sample derived from a biological fluid, like blood, feces, urine. Particular preferred is whole blood, blood serum or blood plasma.

The determination of the expression levels of at least one marker selected from FGF23 and adiponectin in the method of the present invention comprises, inter alia, a quantitative measurement of said marker or said markers.

Quantitative measurement may comprise an immunological assay or an immuno-detection assay. For example, commercial ELISA kits for FGF-23 are currently available from Immutopics US (Cat Number: 60-6500; the exemplified ELISA used in the appended examples) Kainos Laboratories (Cat. Number CY-4000), ALPCA Catalog Number 31-60-6500 or Osteomedical Group (Cat. Number 60-6500). It is evident for the skilled artisan that such assays and test system for the measurement for FGF-23 levels (for example in human or animal serum or plasma) can easily be obtained or generated. The corresponding test systems and assays need corresponding adjustments and evaluation in order to standardize the test for the measurement of "elevated FGF-23 levels". As pointed out above, definitive values are dependent on the test/assay system used.

Such assays are known in the art and may comprise EIA (Enzyme Immuno Assay), FIA (Fluorescent Immuno Assay), and CLIA (Chemiluminescent Immune Assay) or Western Blots.

As illustrated in the appended examples, an elevated expression level of FGF23 and/or adiponectin as compared to a standard control or a reference sample is in particular indicative for the progression of said chronic kidney disease.

The inventive method described herein is in particular of relevance when an elevated level of at least 100 rU/ml (with the specific assay system from Immutopics US (Cat Number: 60-6500) employed in the appended examples this value is 104 rU/ml) are measured since said elevated level of FGF23 protein is predictive for a fast progression of said chronic kidney disease. Again, the specific numerical value is dependant on the test system used and needs to be compared to the data provided herein and/or needs to be validated with healthy controls/healthy control samples. Accordingly, also higher or lower numerical values for the FGF-23 concentration (e.g. in plasma or serum) can be predictive for the faster progression of CKD, as long as this level is elevated in comparison to (a) (healthy) control(s)/control sample(s).

In accordance with the present invention an elevated level of at least 3 μg/ml (with the specific test/assay system used in the experimental part, namely the "Human Adiponectin (Acrp 30) Quantikine ELISA Kit form R&D Systems a value of 4 μg/ml) of adiponectin protein in human male subjects is predictive for a fast progression of said chronic kidney disease. As for FGF-23 discussed herein above, the specific numerical value is dependant on the test system used and needs to be compared to the data provided herein and/or needs to be validated with healthy controls/healthy control samples. Accordingly, also higher or lower numerical values for the adiponectin concentration (e.g. in plasma or serum) can be predictive for the faster progression of CKD, as long as this level is elevated in comparison to (a) (healthy) control(s)/control sample(s) Even if the present invention provides for very reliable markers for the progression of CKD, the inventive method may further comprise the measurement of further, additional markers or of further, additional physiological parameters, like a determination of the glomerular filtration rate.

Said glomerular filtration rate may be determined by use of the iohexyl or iothalamate clearance technique, as also illustrated in the appended examples or by calculation such as by the Cockcroft and Gault formula (Cockcroft (1976) Nephron 16, 31-41), or the MDRD formula (Lhotta (2005) Deutsche Medizinische Wochenschrift 130:2021-24). Such methods are well known in the art, see, inter alia Brenner and Rector "The Kidney" (2004), loc. cit.

In the art, the glomerular filtration rate is considered predictive for the progression of said chronic kidney disease. This means the worse the kidney function estimated by the glomerular filtration rate is at the time of examination (meaning the lower the GFR is), the higher is the probability of a progression of said chronic kidney disease. As illustrated tables provided herein, a patient having a GFR that is 10 ml/min/1.73 m$^2$ higher in comparison to another test person has a probability to show a progression probability of 0.80, i.e. a 20% lower probability to experience a progression of the disease during the investigated observation period. Taken together, accordingly, the data in tables provided herein below show that a patient having a GFR which is 10 ml/min/1.73 m$^2$ lower in comparison to another test person has a 20% higher probability to experience a progression of the disease during the investigated observation period. The person skilled in the art is fully aware that the glomerular filtration rate may be corrected for age and/or sex of the person to be tested; see also "Comprehensive Clinical Nephrology" 3d edition (2007) Feehally, Floege and Johnson.

Another additional measurement of further markers or of further physiological parameters may comprise the determination of the expression level and/or protein level of apolipoprotein A-IV (ApoA-IV).

An elevated ApoA-IV concentration of at least 3 mg/dl is predictive for the progression of said chronic kidney disease.

As documented herein, multiple Cox regression analysis (for COX regression analysis see, inter alia, David (1999) "Applied Survival Analysis-Regression Modeling of Time to Event Data"; Wiley Series in "Probability and Statsitics") clearly showed that the measurement of adiponectin as well as FGF23 showed significant additional information besides the well known association of GFR with progression of kidney disease. Therefore the additional measurement of both parameters adds each on its own additional information. The information provided herein already adjusted for the effects of GFR and is therefore independent of the GFR effects.

The association of Fibroblast growth factor 23 (rU/mL) with progression of kidney disease during the observation period using a multiple Cox Proportional Hazards regression model is provide in the following, illustrative table:

| Variable (increment) | HR (95% CI)* | p |
|---|---|---|
| FGF23 (10 rU/mL) | 1.02 (1.01-1.03) | <0.001 |

*Estimate adjusted for age, sex, glomerular filtration rate and proteinuria

The association of different variables with progression of kidney disease during the observation period using a multiple Cox Proportional Hazards regression model is provide in the following, illustrative table:

| Variable (increment) | HR (95% CI)* | p |
|---|---|---|
| GFR (10 mL/min/1.73 m$^2$) | 0.80 (0.70-0.92) | 0.001 |
| Proteinuria (1 g/24 h/1.73 m$^2$) | 1.29 (0.98-1.69) | 0.07 |
| FGF23 (10 rU/mL) | 1.015 (1.007-1.023) | <0.001 |
| ADMA (1 µmol/l) | 1.65 (1.24-2.19) | 0.001 |

*Estimates are adjusted for age, sex, glomerular filtration rate, proteinuria, Fibroblast growth factor 23, ADMA To the table above: in this statistical model simultaneously containing FGF23 and ADMA, both parameters are independently predicting progression. The hazard ratios (HRs) are already adjusted for the other factors in the model. For example, an increase in FGF23 levels of 10 rU/mL increases the risk of progression by 1.5% (HR of 1.015). Considering that patients with progression of CKD have 260 rU/ml higher FGF23 values compared to those without progression of disease (351 vs. 92 rU/ml), an increase in risk of 39% (26*1.5%) can be expected. The very small p-value of <0.001 also indicates the high predictive value of FGF23. A p-value should generally be lower than p≦0.05 in order to be considered as statistically significant.

The association of adiponectin (µg/mL) with progression of kidney disease during the observation period using a multiple Cox Proportional Hazards regression model in males is provide in the following, illustrative table:

| Variable (increment) | HR (95% CI)* | p |
|---|---|---|
| Adiponectin (1 µg/mL) | 1.16 (1.08-1.23) | <0.001 |

*Estimate adjusted for age, glomerular filtration rate and proteinuria.

The association of different variables with progression of kidney disease during the observation period using a multiple Cox Proportional Hazards regression model in males is provide in the following, illustrative table:

| Variable (increment) | HR (95% CI)* | p |
|---|---|---|
| GFR (10 mL/min/1.73 m$^2$) | 0.79 (0.67-0.94) | 0.01 |
| Proteinuria (1 g/24 h/1.73 m$^2$) | 1.20 (0.87-1.66) | 0.26 |
| Adiponectin (1 µg/mL) | 1.14 (1.07-1.22) | <0.001 |
| FGF23 (10 rU/mL) | 1.014 (1.004-1.025) | 0.01 |
| ADMA (1 µmol/l) | 1.73 (1.18-2.52) | 0.01 |

*Estimates are adjusted for age, glomerular filtration rate, proteinuria, Adiponectin, Fibroblast growth factor 23, and ADMA Comment to the table above: These analyses are conducted in men, because adiponectin values are mostly significant in this group. This table shows a statistical model simultaneously containing FGF23, ADMA, and adiponectin. These three parameters are independently predicting progression. Therefore, the measurement of all three parameters provides for the maximum of information. If one wants to calculate the risk of a patient, when adiponectin, ADMA and FGF23 are 1 increment higher than in another patient, who has no such an elevation, the calculation is a follows: 1.14*1.014*1.73=1.99. The hazard ratios (HRs) are already adjusted for the other factors in the model. For example, an increase in adiponectin levels of 1 µg/mL increases the risk of progression by 14% (HR of 1.14). The very small p-value of <0.001 also indicates the high predictive value of adiponectin. A p-value should generally be lower than p≦0.05 in order to be considered as statistically significant Also provided herein is the use of a specific detection molecule for FGF23 or use of a specific detection molecule for adiponectin for the preparation of a diagnostic composition for the detection of chronic kidney disease or the progression of chronic kidney diseases in a subject suspected to suffer from said disease.

Said detection molecule may be selected from the group consisting of an antibody, an antibody fragment, an antibody derivative, an aptamer.

In a particular preferred embodiment of the means, methods and uses disclosed herein, the said detection molecule is an antibody for FGF-23. Such antibodies are known in the art and, inter alia comprised in the assay commercially available from: Immutopics Inc., San Clemente, USA; (Cat, Number 60-6500). Adiponectin was measured with an ELISA (R&D Systems, Minneapolis, Minn.)).

Also preferred, in embodiments related to the detection of the expression level/quantity of adiponectin an antibody for the detection of adiponectin as provided by R&D Systems as "Human adiponectin (Acrp30) Quantikine ELISA kit.

Again, it is within the normal skills of the artisan to establish and provide for binding molecules, like antibodies, which can easily be used in test assays/test systems for the detection and in particular quantification of the protein level of FGF 23 and/or adiponectin, in particular in (human) serum and plasma probes.

A further embodiment the invention, the use of FGF23 and/or of adiponectin as an in vitro marker for the progression of a chronic kidney disease is provided. In particular it is envisaged that kits are provided wherein FGF-23 and/or adiponectin are to be measured (for example with immunological/immunobiochemical tests, like ELISA) in order to deduce whether a given patient is likely to suffer from a faster progression of chronic kidney disease. Accordingly, also provided is a kit comprising a specific detection molecule for FGF23 or a specific detection molecule for adiponectin for use in the inventive method for the detection of (fast or faster) progression of kidney disease.

Advantageously, the kit of the present invention further comprises, optionally (a) reaction buffer(s), storage solutions and/or remaining reagents or materials required for the conduct of scientific or diagnostic assays or the like. Furthermore, parts of the kit of the invention can be packaged individually in vials or bottles or in combination in containers or multicontainer units.

The kit of the present invention may be advantageously used as diagnostic kits, as research tools or therapeutic tools. Additionally, the kit of the invention may contain means for detection suitable for medical and/or diagnostic purposes. The manufacture of the kits follows preferably standard procedures which are known to the person skilled in the art.

The figures show:

FIG. 1: Receiver operating characteristics (ROC) curve of glomerular filtration rate (GFR) and plasma fibroblast growth factor 23 (FGF23) concentrations with progression of kidney disease as status variable. The area under the curve (AUC) is only slightly larger for GFR than for FGF23 (0.84 and 0.81, respectively).

Figure 2:
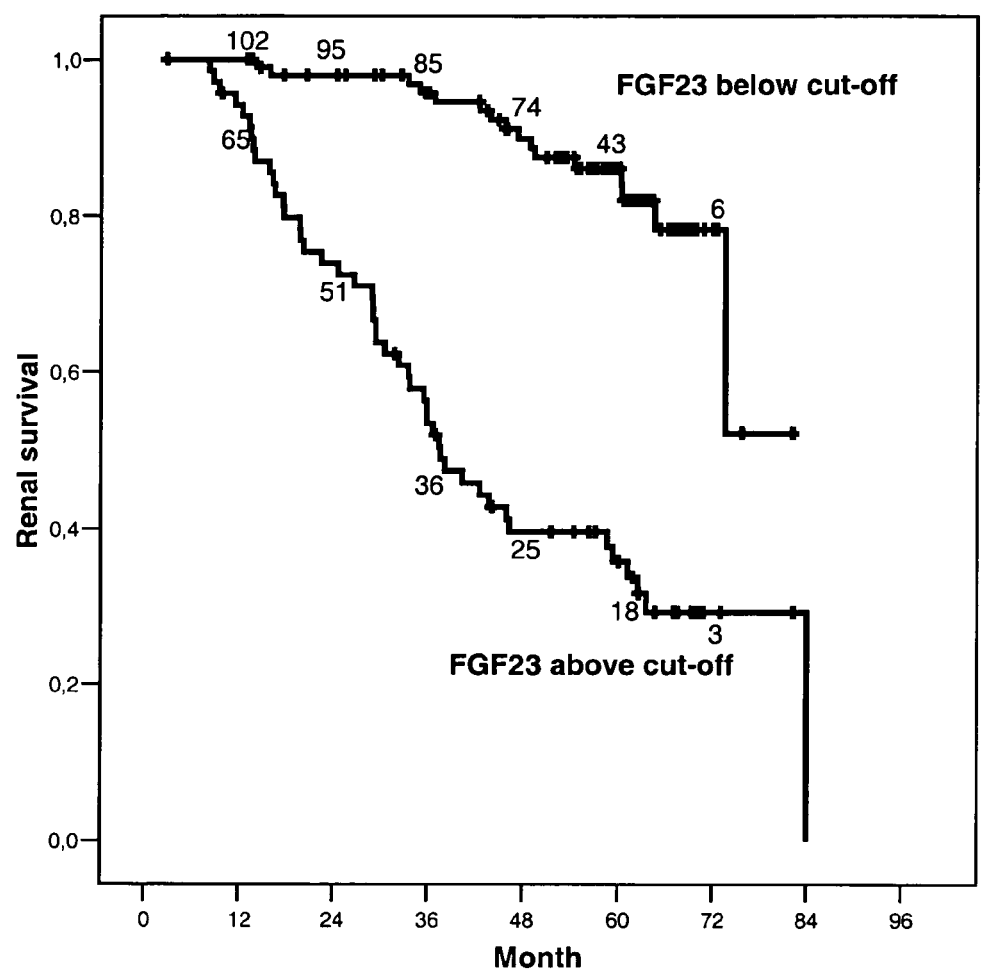

FIG. 2: Kaplan-Meier curves of renal endpoints in patients with below and above optimal cut-off of plasma fibroblast growth factor 23 (FGF23) concentrations. In patients with FGF23 levels above the optimal cut-off (i.e. above 104 rU/mL) progression was significantly faster (log-rank test, p<0.0001). Numbers near the survival curves represent the number of patients at risk with FGF23 levels below and above the optimal cut-off at the times 0, 12, 24, 36, 48, 60 and 72 months.

Figure 3:
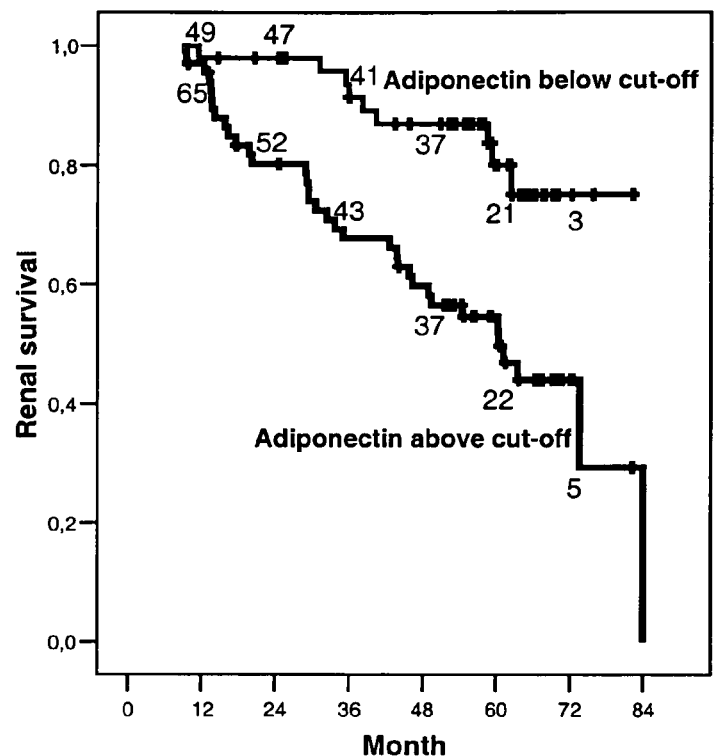
Figure 3:
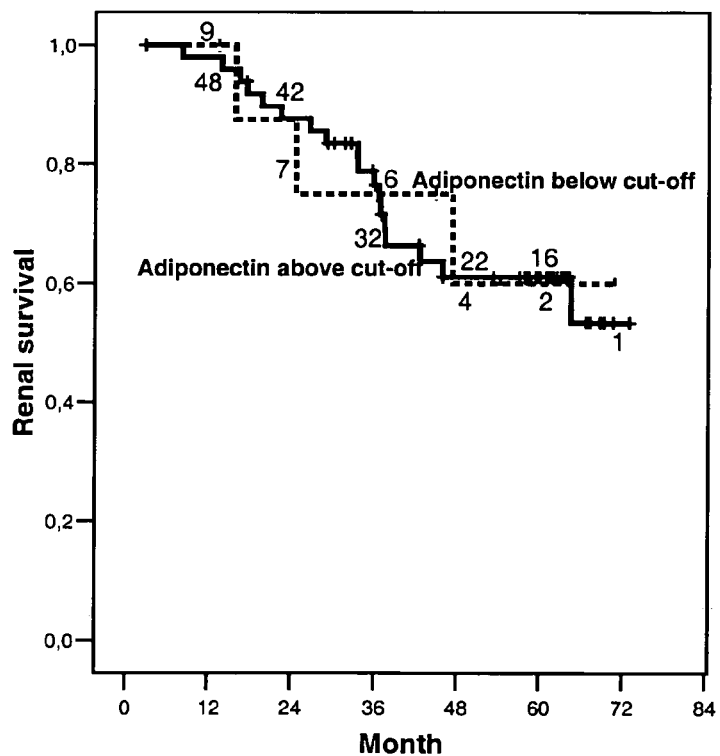

FIG. 3: Kaplan-Meier curves of renal endpoints in male (upper panel) and female (lower panel) patients with plasma adiponectin concentrations above and below the sex-specific cut-off of 4 µg/mL. Male patients with adiponectin levels above the cut-point showed a significantly faster progression than those below this value (log-rank test, p=0.0005). No significant difference was observed in women (p=0.92). Numbers near the survival curves represent the number of patients at risk with plasma adiponectin levels below and above the cut-off at the times 0, 12, 24, 36, 48, 60 and 72 months.

Figure 4:
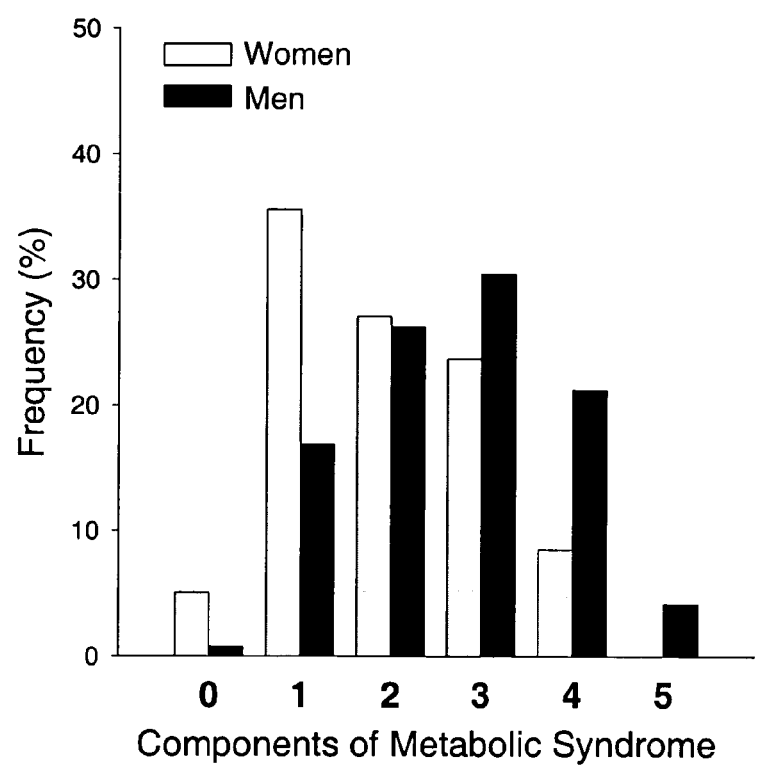

FIG. 4: Frequency of patients according to the concomitant number of components of the metabolic syndrome stratified by gender. In male patients significantly more components of the metabolic syndrome were present as compared to women (Mantel-Haenszel test: $\chi^2$=15.0, df=1, p=0.0001). The factors considered in this analysis are listed in the footnote of Table 1.

FIG. 5A-E: Exemplary coding sequence and corresponding amino acid sequence of human FGF23 (SEQ ID NO:1 and SEQ ID NO:2)

FIG. 6A-H: Exemplary coding sequence and corresponding amino acid sequence of human adiponectin (SEQ ID NO:7 and SEQ ID NO:8)

The examples show:

EXAMPLE I

Methods for Evaluation of FGF23 as a Parameter for CKD

Patients and Baseline Investigations

We examined at baseline 227 Caucasian patients aged between 18 and 65 years with non-diabetic CKD and various degrees of renal impairment. These patients were recruited from 8 nephrology departments in Germany, Austria and South Tyrol (Italy) as described earlier (Boes, (2006) J. Am. Soc. Nephrol. 17, 528-536). The study was approved by the institutional Ethic Committees, and all subjects gave written informed consent. They had stable renal function for at least 3 months before entry into the study. Exclusion criteria were treatment with immunosuppressive agents, fish oil or erythropoietin, serum creatinine above 6 mg/dL, diabetes mellitus of any type, malignancy, liver, thyroid or infectious disease, nephrotic syndrome (defined as proteinuria >3.5 g/1.73 m$^2$/day), organ transplantation, allergy to ionic contrast media and pregnancy. According to the National Kidney Foundation (NKF) classification of CKD, our study cohort showed the following stages of CKD: GFR≧90 mL/min/1.73 m$^2$ (stage 1) in 72 patients (31.7%), GFR≧60-89 mL/min/1.73 m$^2$ (stage 2) in 49 patients (21.6%), GFR≧30-59 mL/min/1.73 m$^2$ (stage 3) in 63 patients (27.8%), GFR<30 mL/min/1.73 m$^2$ (stage 4+5) in 43 patients (18.9%). The primary cause of kidney disease was glomerulonephritis in 97 (biopsy-confirmed in 90) patients, adult polycystic kidney disease in 37 patients, interstitial nephritis in 24 patients, other types of kidney disease in 43 patients and unknown in 26 patients.

In order to avoid inter-observer differences, all patients were recruited by one physician who visited all participating centers. Patient history, including smoking habits and antihypertensive treatment at baseline, was recorded by interview and confirmed by checking patient records. This was complemented by clinical examination including assessment of body mass index (BMI) and blood pressure. Hypertension was defined as blood pressure above 140/90 mm Hg and/or the use of antihypertensive medication. We also calculated pulse pressure as the difference between systolic and diastolic blood pressure. Antihypertensive medication was withheld on the day of the study in order to minimize interference with measurements of the GFR. Antihypertensive drugs were taken by 179 patients (79%): diuretics (n=83; 37%), ACE-inhibitors (n=123; 54%), calcium channel blockers (n=78; 34%), beta receptor blockers (n=67; 30%) and alpha-1 receptor blockers (n=36; 16%).

Prospective Follow-Up

After the baseline investigation patients were followed prospectively until the primary study endpoint or the end of the observation period was reached. The primary endpoint was defined as doubling of baseline serum creatinine and/or terminal renal failure necessitating renal replacement therapy. A total of 177 patients (78%) from the baseline cohort could be assessed during the follow-up. Patients lost to follow-up (n=50) had at baseline a significantly better renal function than patients not lost for follow-up, i.e. a higher mean GFR (91±44 vs. 64±39 mL/min/1.73 m$^2$; p<0.01). However, both groups did not differ significantly with respect to age and gender. Patients lost to follow-up had moved away or were not referred by their physicians for follow-up visits in the renal units.

Laboratory Measurements

Blood samples for measurement of routine chemistry, high sensitivity C-reactive protein (hsCRP), PTH and FGF23 were taken after an overnight fast of at least 12 hours. The samples were immediately centrifuged at 1.500 g and 4° C. for 10 minutes, and the supernatants stored in aliquots at −80° C. until further use. PTH was measured with an immuno-radiometric assay (IRMA), and FGF23 was measured using the human C-terminal enzyme-linked immunosorbent assay (ELISA) (Immutopics Inc., San Clemente, USA) (Weber, (2003) J. Bone Miner Res. 18, 1227-1234). The inter-assay coefficients of variability for the latter are 6.5% at 40 rU/mL, and 7.5% at 175 rU/mL respectively, and the lower detection limit is 3.0 rU/mL.

Measurements of routine chemistry including hsCRP were performed with routine laboratory tests. In addition, GFR was assessed in all patients using the iohexyl clearance technique as described in Bostom, (2002) J. Am. Soc. Nephrol. 13, 2140-2144.

Statistical Analysis

Statistical analysis was performed with Statistical Package for the Social Sciences (SPSS) for Windows 12.01. Univariate comparisons of continuous variables between various groups were performed using an unpaired t test or the nonparametric Wilcoxon rank sum test in case of non-normally distributed variables. Dichotomized variables were compared using Pearson's $\chi^2$-test. Differences were considered as significant at p<0.05. Data are presented as mean±SD or as median and $25^{th}$ and $75^{th}$ percentile for skewed variables. Univariate correlation analysis was performed by Spearman correlation analysis. Kaplan-Meier time-to-event curves were generated for patients with FGF23 concentrations above and below the Receiver Operating Characteristics (ROC) analysis-derived optimal cut-off of 104 rU/mL. Multiple adjusted risk estimates for progression endpoints were calculated using a Cox proportional hazards regression analysis.

EXAMPLE II

Stages of CKD and Calcium-Phosphate Metabolism and Corresponding Progression of CKD Baseline clinical characteristics and laboratory data of 227 CKD patients are reported in Table 1. In order to elucidate the relationship between renal function and parameters of calcium-phosphate metabolism, renal patients were stratified into four groups according to NKF criteria for renal failure: GFR≧90 ml/min/1.73 m², GFR≧60-89 ml/min/1.73 m², GFR≧30-59 ml/min/1.73 m², and GFR<30 ml/min/1.73 m² (Table 1). A continuous and significant increase of calcium× phosphate product, PTH and FGF23 concentrations across the different NKF stages of renal dysfunction was found. In addition, serum phosphate was significantly higher in patients with more advanced renal failure. Furthermore, a significant correlation between GFR on the one hand and FGF23 (r=−0.61, p<0.001), PTH (r=−0.70, p<0.001), and serum phosphate (r=−0.46, p<0.001) levels on the other hand was found.

Clinical characteristics and laboratory data of patients with follow-up are reported in Table 2. The median follow-up after completion of the baseline investigation was 53 [3-84] months. During the follow-up 65 patients had progressed to a renal endpoint: 36 patients had doubled their serum creatinine and 29 patients had reached terminal renal failure necessitating renal replacement therapy. Those patients who had reached a progression endpoint were significantly older, had higher protein excretion rates as well as lower GFR. In addition, they had significantly higher phosphate, PTH and FGF23 levels, and calcium×phosphate product. There were no differences for surrogate parameters of nutritional (BMI, albumin) and inflammatory status (hsCRP). Age and sex-adjusted Cox regression analysis revealed that GFR and FGF23 showed a strong association with progression-free survival besides other parameters of the calcium-phosphate metabolism (phosphate, calcium×phosphate product and PTH) (Table 3, Model 1). When further models were calculated with an extended adjustment for all five variables from model 1, and age and gender, only baseline GFR [hazard ratio 0.767; 95% confidence interval (CI) 0.668-0.880 for an increment of 10 mL/min/1.73 m²; p<0.0001] and plasma FGF23 concentrations [hazard ratio 1.013; 95% CI 1.005-1.022 for an increment of 10 rU/mL; p=0.003] were significantly associated with progression during the follow-up period. Serum calcium, phosphate and PTH concentrations were not independently associated with disease progression (Table 3, model 2). When only parameters of the calcium-phosphate metabolism was used without FGF23 levels in a third model PTH was observed, besides baseline GFR, to predict CKD progression. Finally, for each of the parameters of the calcium-phosphate metabolism the estimates for CKD progression was calculated, adjusted for age, sex, GFR and proteinuria (Table 4): it was observed that PTH, phosphate, and calcium×phosphate product but not calcium predicted disease progression.

To evaluate the significance of FGF23 as predictor for the progression of kidney disease, a ROC analysis for FGF23 in comparison to GFR was performed (FIG. 1). The area under the curve (AUC) was only slightly larger for GFR [AUC=0.84; 95% CI: 0.78-0.90; p<0.001] than for FGF23 [AUC=0.81; 95% CI: 0.74-0.88; p<0.001]. Kaplan-Meier curves of progression-free survival comparing patients with FGF23 values above and below the optimal cut-off level of 104 rU/mL were constructed. It was surprisingly found that patients with FGF23 levels above this value had a worse prognosis and significantly faster progression to the endpoint compared to those with FGF23 levels below this threshold (FIG. 2). The mean follow-up time to a progression endpoint was 46.9 [95% CI: 40.2-53.6] months compared to 72.5 [95% CI: 67.7-77.3] months (p<0.0001). Similar survival curves were observed when the median of FGF23 (85 rU/mL) was used instead of the ROC-derived cut-off of 104 rU/mL (data not shown).

EXAMPLE III

FGF23 as a Novel Risk Marker for the Progression of CKD

The results of this prospective long-term study (see Examples I and II) in a sizable cohort of Caucasian patients with non-diabetic CKD have identified FGF23 as a novel risk marker for the progression of CKD. Remarkably and surprisingly, apart from baseline GFR, FGF23 was the only independent predictor of progression among several parameters of calcium-phosphate metabolism assessed.

FGF23 is a recently identified "phosphatonin" which is thought to be implicated in the systemic balance of phosphate maintained by the interaction of intestine, bone and the kidneys (Berndt, (2005) loc. cit.; Weber, (2003), loc. cit.; Fugakawa, (2005) Nephrol. Dial. Transplant 20, 1295-1298). In several clinical conditions excessive activity of FGF23 resulted in hypophosphatemia, low 1,25-OH$_2$D$_3$ levels and osteomalacia (ADHR Consortium, (2000) Nat. Genet. 26, 345-348; Jonsson, (2003) N. Engl. J. Med. 348, 1656-1663). In addition, administration of recombinant FGF23 to experimental animals or overexpression of the FGF23 gene in-vivo produced similar derangements of calcium-phosphate metabolism, while inactivation of this gene caused hyperphosphatemia and high circulating 1,25-OH$_2$D$_3$ levels (Shimada, (2001) Proc. Natl. Acad. Sci. USA 98, 6500-6505; Shimada, (2004) Biochem. Biophys. Res. Commun. 314, 409-141; Shimada, (2004) J. Clin. Invest. 113, 561-568). It was speculated that the physiological stimulus for FGF23 secretion is hyperphosphatemia caused by a dietary phosphate load (Ferrari, (2005) J. Clin. Endocrinol. Metab. 90, 1519-1524). The increase in FGF23 levels in response to dietary phosphate promotes phosphaturia and suppresses renal production of active vitamin D. Thus, a significant physiological role for FGF23 in phosphate homeostasis is postulated with the intact kidney as one of the major target organs (Weber, (2003), loc. cit.; Fugakawa, (2005), loc. cit.). However, in the presence of progressive CKD serum FGF23 levels increase in parallel with the deterioration of renal function and an increase of serum phosphate and PTH concentrations (Berndt, (2005), loc. cit.; Larsson, (2003) Kidney Int. 64, 2272-2279; Imanishi, (2004) Kidney Int. 65, 1943-1946; Shigematsu, (2004) Am. J. Kidney Dis. 44, 250-256). In pre-dialysis patients and in patients on maintenance hemodialysis, high FGF23 serum levels were correlated with those of phosphate, pointing to a deranged feedback loop resulting in very high levels of serum FGF23. The decrease of renal function across a wide range of GFR is paralleled by a an increase in serum FGF23 concentrations (Table 1) Moreover, in experimental studies the increase of FGF23 levels preceded the decrease of serum 1,25-$OH_2D_3$ concentrations, suggesting an important role of FGF23 in the development of secondary hyperparathyroidism in patients with CKD. Collectively these experimental and our clinical data implicate that circulating FGF23 is a physiological regulator of phosphate balance, and as such also a potential uremic toxin (Weber, (2003), loc. cit.; Fugakawa, (2005), loc. cit.).

It is of interest that PTH, phosphate and calcium×phosphate product, were independently associated with progression only when FGF23 was not included in the Cox regression models (see Table 4 and model 3 in Table 3). This finding underscores that disturbances of the calcium-phosphate metabolism and probably not direct effects of FGF23 seem to be involved in CKD progression. In other words, FGF23 is an excellent indicator of the complex changes in calcium-phosphate metabolism induced by CKD, and probably also a very suitable surrogate parameter of the sequelae of these metabolic alterations. This may be clinically important: it has been known for decades that in endstage renal disease hyperphosphatemia causes soft tissue calcification including vascular calcification (Ibels, (1979) Am. J. Med. 66, 790-796). The latter comprises mainly calcification of intimal plaques and of the media of central arteries (Mönckeberg sclerosis) (Schwarz, (2000) Nephrol. Dial. Transplant. 15, 218-223). However, until recently the impact on survival of increased serum phosphate levels in patient with CKD was not well appreciated. In 1998 Block (Am. J. Kidney Dis. 31, 607-617) it was found that in dialysis patients survival was significantly less if pre-dialysis serum phosphate concentration exceeded 6.5 mg/dl.

This increase was related to death from coronary heart disease, possible due to accelerated coronary plaque calcification in this population (Ganesh, (2001) J. Am. Soc. Nephrol. 12, 2131-2138). Phosphate, more specifically intracellular phosphate, plays a major role in the genesis of vascular calcification, particularly in the presence of ionised calcium (Giachelli, (2005) Circ. Res. 96, 717-722). However, the adverse role of high serum phosphate concentrations is not restricted to patients with end-stage renal failure (Kestenbaum, (2005) J. Am. Soc. Nephrol. 16, 520-528), and even in non-renal patients serum phosphate concentrations were positively and significantly correlated to the severity of coronary artery disease and to the severity of coronary artery stenoses and presence of occlusions (Narang, (1997) Int. J. Cardiol. 60, 73-79). In a post-hoc analysis of the CARE study in 4,127 patients, Tonelli et al found that serum phosphate levels (even within the upper normal range) are associated with more adverse cardiovascular outcomes (Tonelli, (2005) Circulation 112, 2627-2633). They also found a direct association between GFR and serum phosphate concentrations, but the relation between phosphate and outcome still persisted when individuals with a GFR below 60 ml/min were excluded from the analysis. Interestingly, the calcium×phosphate product was not independently associated with adverse outcome (Tonelli, (2005), loc. cit.). Taken together, these data suggest that even minor derangements in the calcium-phosphate metabolism, and particularly in serum phosphate levels, may contribute to cardiovascular complications in non-renal patients as well as in patients with CKD. The present study adds to the possibility that serum phosphate levels may impact on progression of renal disease as well, as suggested by the experimental work of Haut and Alfrey (Haut, (1981) Kidney Int. 17, 722-731; Alfrey, (2004) Kidney Int. Suppl. 90, S13-S17), and to our knowledge is the first large prospective study investigating the influence of changes in calcium-phosphate metabolism and the role of FGF23 in CKD progression. Given the physiological role of FGF23 in phosphate metabolism, this "phosphatonin" is, in accordance with this invention, an excellent indicator of cardiovascular risk not only in CKD patients. Further studies on this issue are warranted.

In summary, in the present prospective study it was found that disturbed calcium-phosphate metabolism affects progression in patients with non-diabetic CKD and FGF23 was identified as a novel predictor for CKD progression. Thus, early correction of alterations in the calcium-phosphate metabolism could be a valuable clinical approach to modify progression of CKD, and FGF23 is a clinically useful risk indicator of progression of CKD.

EXAMPLE IV

Materials and Methods in the Following Adiponectin Study

As in Examples I to III, 227 Caucasian patients aged between 18 and 65 years with non-diabetic CKD and various degrees of renal impairment were examined; see also Example I. The same criteria applies here, mutatis mutandis.

The prospective follow-up and definition of renal endpoints was also described in Example I. Also here a total of 177 patients (78%) from the baseline cohort could be assessed during the follow-up. Patients lost to follow-up (n=50) had significantly better renal function than patients not lost for follow-up, but both groups did not differ significantly with respect to age and gender (data not shown).

Laboratory Measurements in the Adiponectin Study

Blood samples for the measurement of adiponectin and other parameters were taken after an overnight fast of at least 12 hours. Adiponectin plasma concentrations were measured with an ELISA (R&D Systems, Minneapolis, Minn.). Glomerular filtration rate (GFR) was assessed in all patients using the iothalamate clearance technique as described in detail elsewhere (Bostom, (2002), loc. cit.). Criteria for clinical diagnosis of metabolic syndrome were defined according to the scientific statement from the American Heart Association (AHA) and the National Heart, Lung, and Blood Institute (NHLBI) (Grundy, (2005) Circulation 112, 2735-2752). The insulin sensitivity in the patients was also quantified, using the Homeostasis Model Assessment of Insulin Resistance (HOMA-IR): plasma insulin (mU/L)×plasma glucose (mg/dL)÷405.

Statistical Analysis

Comparisons of variables between various groups were performed using unpaired t-tests, nonparametric Wilcoxon rank sum tests and Pearson's $\chi^2$-test. Kaplan-Meier time-to-event curves were generated for patients with serum adiponectin concentrations above and below the gender-specific Receiver Operating Characteristics (ROC) analysis-derived optimal cut-off of adiponectin and hazard ratios for progression were estimated using a Cox proportional hazards regression model adjusted for age and other risk factors of disease progression.

EXAMPLE V

Adiponectin as Marker of CKD Progression in Men

Baseline clinical characteristics and laboratory data of the patients with follow-up are reported in the first column of Table 5. The median follow-up after completion of the baseline investigation was 53 [minimum-maximum 3-84] months. During follow-up, 65 patients progressed to a renal endpoint. Table 1 further presents data of patients with and without disease progression. Patients who had reached a progression endpoint were significantly older, had higher baseline serum creatinine and adiponectin levels and protein excretion rates as well as lower GFR. In addition, more components of the metabolic syndrome were present in these patients (p<0.005). Age- and sex-adjusted as well as an extended adjusted Cox regression analysis revealed high adiponectin levels as a significant predictor of disease progression (Table 6). A metabolic syndrome was not a significant factor for disease progression (p=0.082). An interaction term between adiponectin concentrations and gender was highly significant (p=0.001). Therefore, all further analyses were stratified for men and women.

In women, adiponectin concentrations were not a significant predictor in either model, whereas in men, adiponectin was a significant predictor of disease progression in all models (p<0.0001) (part 2 of Table 6). Adiponectin levels were still significantly associated with disease progression in men even when adjusted for asymmetric dimethylarginine or apolipoprotein A-IV, which was recently shown to be significant predictors of progression (Boes, (2006, loc. cit.; Fliser, (2005) J. Am. Soc. Nephrol. 16, 2456-2461). Metabolic syndrome, insulin, and HOMA-IR were not associated with disease progression. The same holds true for the type of renal disease as well as the use or kind of antihypertensive medications when adjusted for baseline GFR (data not shown). It was further observed that male patients in the lowest compared to the highest tertile of BMI showed a clear trend to higher adiponectin levels (6.55±4.30 vs. 5.31±4.52, p=0.098) and a higher probability of disease progression (HR (95% CI) 2.46 (1.03-5.89), p=0.043).

Separately for men and women, Kaplan-Meier curves of the progression-free survival comparing patients with high versus low serum adiponectin concentrations using the gender-specific optimal cut-off were constructed. This optimal cut-off was derived from ROC analysis and was 4 µg/mL for both genders. Male patients with adiponectin levels above this threshold had a worse prognosis and significantly faster progression to the endpoint compared to those with adiponectin levels below this threshold (log-rank test, p=0.0005), (FIG. 3A): the mean follow-up time to a progression was 54.9 (95% CI: 47.8-62.0) months compared to 73.2 (95% CI 67.8-78.6) months, respectively. In women, there was no evidence for a difference in progression-free survival in relation to the adiponectin level (FIG. 3B). The results for both genders did not change markedly using the gender-specific median instead of the ROC-derived optimal cut-off of adiponectin levels.

Men suffered more often from a metabolic syndrome (56% vs. 32%, p=0.003) and had significantly more components of the metabolic syndrome compared to women (2.67±1.14 vs. 1.95±1.07, p<0.001) (FIG. 2).

This prospective study in patients with non-diabetic primary CKD identified high adiponectin levels as a novel predictor of CKD progression in men, but not in women, independent of other predictors of disease progression.

Adiponectin levels increase with impaired kidney function (Zoccali, (2002), loc. cit.; Lee, (2004) Int. J. Artif. Organs 27, 835-841). Potential mechanistic explanations are changes in the ligand/receptor reactivity as shown for other hormone/receptor systems in renal failure (Shen, (2005) Nephrology (Carlton) 10, 599-605), reduced adiponectin clearance by the kidney (Isobe, (2005) Eur. J. Endocrinol. 153, 91-98) or a counter-regulatory response to metabolic derangements in renal failure (Zoccali, (2003), Kidney Int. Suppl. 84, S98-S102).

The finding of high adiponectin levels as predictor of CKD progression, at least in men, was unanticipated considering that low adiponectin levels were associated with obesity, type 2 diabetes mellitus and cardiovascular disease in the general population. In contrast to these cross-sectional findings some prospective studies failed to document an association between adiponectin and cardiovascular events (Lawlor, (2005) J. Clin. Endocrinol. 90, 5677-5683; Lindsay, (2005) Arterioscler. Thromb. Vasc. Biol. 25, e15-e16; Shimada, (2002) Jpn Heart 43, 85-91). In agreement with findings provided herein, however, in the study of Kistorp et al. (Kistorp, (2005) Circulation 112, 1756-1762) high adiponectin levels were predictive for mortality in patients with chronic heart failure (CHF), independent of CHF severity. It has recently been suggested that adiponectin increases energy expenditure and induces weight loss through a direct effect on the brain (Fruebis, (2001) Proc. Natl. Acad. Sci. USA 98, 2005-2010; Qi, (2004) Nat. Med. 10, 524-529). It has been proposed that in the context of increased energy expenditure high plasma adiponectin levels might not be beneficial in CHF. And the same is potentially true in renal patients. This would be in line with the observation provided herein that male patients in the lowest tertile of BMI had higher adiponectin levels and were more likely to progress. In this respect CHF and CKD patients may have much in common and many traditional risk factors such as hypercholestrolemia, hypertension or high BMI may provide beneficial outcomes, a well known constellation which is called "reverse epidemiology" (Kalantar-Zadeh, (2006) Semin. Nephrol. 26, 118-133). Patients with CKD often develop CHF (Al Ahmad, (2001) J. Am. Coll. Cardiol. 38, 955-962; McClellan, (2002) J. Am. Soc. Nephrol. 13, 1928-1936), as also indicated by increasing N-terminal pro brain natriuretic peptide (NT-proBNP) levels with decreasing kidney function, found by us and others recently (Luchner, (2005) Hypertension 46, 1-6; DeFilippi, (2005) Am. J. Kidney Dis. 46, 35-44) (Spanaus et al, unpublished results). In the MMKD cohort, a significant correlation exists between NT-proBNP and adiponectin concentrations (r=0.30, p<0.001). Nevertheless, adjusting the Cox regression analysis for NT-proBNP concentrations and GFR had no impact on the association between adiponectin and progression of CKD. It is therefore conceivable that this association of high adiponectin levels with progression of CKD reflects a relationship to prevalent CHF which is not reflected by the values of NT-proBNP as a surrogate parameter for CHF. It could also reflect a functional impairment of the kidney which is less related to diminished glomerular filtration than to other non-filtration-related consequences of kidney dysfunction.

An alternative explanation for the association of high adiponectin levels with progression of CKD in men could be adiponectin resistance (Kadowaki, (2005) Endocr. Rev. 26, 439-451; Furuhashi, (2004) Diabetes Care 27, 2217-2221) caused by dysfunction or downregulation of adiponectin receptors with consecutive counterregulatory increased adiponectin secretion. Such adiponectin resistance might be analogous to the finding of virtually absent uptake of adiponectin across the coronary bed found in diabetic compared to non-diabetic patients (Furuhashi, (2004), loc. cit.).

Adiponectin levels are much less predictive for CKD progression in women although women have significantly higher adiponectin levels compared to men. An explanation for this finding might again be the presence of adiponectin resistance, the latter being more pronounced in men than in women. This assumption is in line with the observation that in our cohort of women a metabolic syndrome was less frequent and the number of components of the metabolic syndrome was lower compared to men. This finding is different from the general population in which the metabolic syndrome tends to be more frequent in women (Reynolds, (2005) Am. J. Med. Sci 330, 273-279). Without being bound by theory, it is speculated that the ligand-receptor interaction might be less disturbed in women compared to men.

In summary, in this prospective 7 years study follow-up in patients with non-diabetic CKD, adiponectin was identified as a novel predictor for CKD progression in men but not in women. This observation is also of relevance for other conditions of progressive vascular sclerosis.

TABLE 1

Baseline clinical and laboratory data of 227 patients stratified according to glomerular filtration rate.

| | GFR ml/min/1.73 m² | | | | |
|---|---|---|---|---|---|
| | >=90 (n = 72) | >=60-89 (n = 49) | >=30-59 (n = 63) | <30 (n = 43) | Overall p-value* |
| Gender (male/female), n (%) | 50/22 (69/31) | 34/15 (69/31) | 44/19 (70/30) | 26/17 (61/40) | 0.72 |
| Age (years) | 39.9 ± 13.2 | 46.1 ± 11.6 | 45.9 ± 11.5 | 54.4 ± 8.5 | <0.0001 |
| Body mass index (kg/m²) | 24.0 ± 3.3 | 25.6 ± 3.8 | 25.4 ± 3.3 | 26.1 ± 4.8 | 0.02 |
| Current smokers, n (%) | 18 (25) | 11 (22) | 11 (18) | 9 (21) | 0.97 |
| Systolic blood pressure (mmHg) | 134 ± 21 | 140 ± 24 | 139 ± 19 | 137 ± 19 | 0.21 |
| Diastolic blood pressure (mmHg) | 84 ± 13 | 88 ± 15 | 88 ± 14 | 88 ± 13 | 0.20 |
| Serum creatinine (mg/dL) | 1.14 ± 0.22 [0.95; 1.11; 1.30] | 1.54 ± 0.45 [1.25; 1.43; 1.70] | 2.31 ± 0.79 [1.70; 2.18; 2.80] | 3.63 ± 1.27 [2.73; 3.50; 4.61] | <0.0001 |
| Glomerular filtration rate (mL/min/1.73 m²) | 120 ± 28 (97; 110; 132) | 74 ± 9 (65; 71; 81) | 44 ± 7 (38; 44; 50) | 19 ± 7 (12; 18; 26) | <0.0001 |
| Proteinuria (g/24 h/1.73 m²) | 0.60 ± 0.66 [0.13; 0.36; 0.82] | 1.10 ± 1.10 [0.16; 0.57; 1.93] | 1.08 ± 0.94 [0.27; 0.81; 1.83] | 1.03 ± 0.81 [0.36; 0.89; 1.52] | 0.004 |
| Serum albumin (g/dL) | 4.70 ± 0.38 | 4.46 ± 0.50 | 4.55 ± 0.38 | 4.53 ± 0.34 | 0.01 |
| High sensitivity C-reactive protein (mg/L) | 0.21 ± 0.27 | 0.32 ± 0.33 | 0.23 ± 0.21 | 0.35 ± 0.38 | 0.01 |
| Fibroblast growth factor 23 (rU/mL) | 57 ± 43 (36; 46; 63) | 81 ± 52 (45; 69; 99) | 187 ± 194 (67; 108; 230) | 456 ± 475 (127; 285; 584) | <0.0001 |
| Calcium (mmol/L) | 2.37 ± 0.11 [2.30; 2.36; 2.43] | 2.40 ± 0.30 [2.30; 2.37; 2.43] | 2.34 ± 0.20 [2.27; 2.37; 2.44] | 2.34 ± 0.20 [2.23; 2.32; 2.46] | 0.63 |
| Phosphate (mmol/L) | 1.02 ± 0.42 [0.85; 0.97; 1.10] | 1.01 ± 0.29 [0.86; 0.97; 1.18] | 1.08 ± 0.23 [0.92; 1.03; 1.18] | 1.32 ± 0.24 [1.19; 1.29; 1.55] | <0.0001 |
| Calcium x phosphate product (mg²/dl²) | 2.40 ± 0.92 [2.02; 2.26; 2.58] | 2.42 ± 0.69 [1.89; 2.39; 2.81] | 2.52 ± 0.51 [2.16; 2.47; 2.83] | 3.10 ± 0.63 [2.74; 2.98; 3.52] | <0.0001 |
| Parathormone (pmol/L) | 3.8 ± 1.5 [2.7; 3.5; 4.9] | 6.8 ± 4.3 [4.6; 5.8; 7.6] | 12.0 ± 9.5 [5.3; 9.5; 17.0] | 27.3 ± 21.6 [13.0; 21.0; 38.0] | <0.0001 |
| Use of vitamin D, n (%) | 0 (0) | 4 (8) | 13 (21) | 13 (30) | <0.0001 |
| Use of a phosphate binder, n (%) | 0 (0) | 2 (4) | 3 (5) | 7 (16) | 0.002 |

*obtained from Kruskal-Wallis test, One-way ANOVA, and Chi-square test, respectively. For skewed variables data are also presented as mean ± SD and 25/50/75 percentiles (where appropriate)

TABLE 2

Clinical and laboratory data of 177 patients with completed follow-up with further stratification to those with and without progression during the follow-up period.

| | Non-progressors (n = 112) | Progressors (n = 65) |
|---|---|---|
| Gender (male/female), n (%) | 74/38 (66%/34%) | 44/21 (68%/32%) |
| Age (years) | 44.8 ± 12.6 | 49.1 ± 11.1[a] |
| Body mass index (kg/m²) | 24.8 ± 3.5 | 25.7 ± 3.9 |
| Current smokers, n (%) | 18 (16%) | 16 (25%) |
| Systolic blood pressure (mmHg) | 136 ± 22 | 137 ± 17 |
| Diastolic blood pressure (mmHg) | 86 ± 14 | 88 ± 12 |
| Serum creatinine (mg/dL) | 1.54 ± 0.61 [1.14; 1.40; 1.80] | 3.21 ± 1.31[d] [2.21; 3.10; 3.94] |
| Glomerular filtration rate (mL/min/1.73 m²) | 79 ± 38 [50; 74; 99] | 38 ± 25[d] [20; 33; 46] |
| Proteinuria (g/24 h/1.73 m²) | 0.87 ± 0.95 [0.14; 0.46; 1.25] | 1.25 ± 0.83[d] [0.61; 1.09; 1.78] |
| Serum albumin (g/dL) | 4.57 ± 0.43 | 4.53 ± 0.36 |
| High sensitivity C-reactive protein (mg/L) | 0.28 ± 0.32 | 0.29 ± 0.31 |
| Fibroblast growth factor 23 (rU/mL) | 92 ± 113 [41; 64; 96] | 351 ± 394[d] [96; 190; 492] |
| Calcium (mmol/L) | 2.38 ± 0.22 [2.30; 2.37; 2.44] | 2.32 ± 0.17[a] [2.24; 2.31; 2.43] |
| Phosphate (mmol/L) | 1.04 ± 0.38 (0.86; 1.01; 1.14) | 1.25 ± 0.27[d] [1.02; 1.23; 1.49] |
| Calcium x phosphate product (mmol²/L²) | 2.46 ± 0.85 (2.00; 2.37; 2.76) | 2.90 ± 0.65[d] [2.43; 2.83; 3.22] |
| Parathormone (pmol/L) | 6.5 ± 5.3 [3.4; 5.0; 7.2] | 22.5 ± 20.0[d] [8.0; 16.0; 29.5] |
| Use of vitamin D, n (%) | 9 (8) | 20 (31)[d] |
| Use of a phosphate binder, n (%) | 2 (2) | 10 (15)[d] |

[a] p < 0.05;
[b] p < 0.01;
[c] p < 0.005;
[d] p < 0.001 - comparison between progressors and non-progressors For skewed variables data are also presented as mean ± SD and 25/50/75 percentiles (where appropriate)

TABLE 3

The association of different variables with progression of kidney disease during the observation period using multiple Cox Proportional Hazards regression models.

| Variable (increment) | Model 1 Adjusted for age and sex HR 95% CI) | p | Model 2 Adjusted for age, sex and all other 7 variables of this table HR (95% CI) | p | Model 3 Adjusted for age, sex and all other 6 variables of this table (but without FGF23) HR (95% CI) | p |
|---|---|---|---|---|---|---|
| GFR (10 mL/min/1.73 m$^2$) | 0.668 (0.590-0.757) | <0.0001 | 0.767 (0.668-0.880) | 0.0002 | 0.742 (0.650-0.847) | <0.0001 |
| Proteinuria (1 g/24 h) | 1.298 (1.023-1.647) | 0.032 | 1.240 (0.916-1.680) | 0.165 | 1.134 (0.852-1.510) | 0.390 |
| Calcium (0.1 mmol/L) | 0.885 (0.746-1.049) | 0.159 | 0.578 (0.265-1.259) | 0.168 | 0.598 (0.278-1.283) | 0.187 |
| Phosphate (0.1 mmol/L) | 1.091 (1.049-1.134) | <0.0001 | 0.401 (0.112-1.434) | 0.160 | 0.421 (0.124-1.436) | 0.167 |
| Ca × P product (0.1 mmol$^2$/L$^2$) | 1.041 (1.022-1.061) | <0.0001 | 1.528 (0.876-2.664) | 0.135 | 1.519 (0.888-2.599) | 0.127 |
| Parathormone (1 pmol/L) | 1.041 (1.029-1.052) | <0.0001 | 1.010 (0.994-1.025) | 0.214 | 1.018 (1.004-1.032) | 0.014 |
| FGF23 (10 rU/mL) | 1.028 (1.021-1.034) | <0.0001 | 1.013 (1.005-1.022) | 0.003 | | |

GFR = glomerular filtration rate;
FGF23 = fibroblast growth factor 23;
Ca × P product = calcium × phosphate product.

TABLE 4

The association of variables of the calcium-phosphate metabolism with progression of kidney disease during the observation period using multiple Cox Proportional Hazards regression models. Fibroblast growth factor 23 (FGF23) was not included in these models.

| Variable | HR (95% CI)* | p |
|---|---|---|
| Calcium (0.1 mmol/L) | 0.964 (0.835-1.113) | 0.62 |
| Phosphate (0.1 mmol/L) | 1.124 (1.041-1.214) | 0.003 |
| Calcium × phosphate product (0.1 mmol$^2$/L$^2$) | 1.054 (1.017-1.092) | 0.004 |
| Parathormone (1 pmol/L) | 1.023 (1.010-1.036) | 0.001 |

*Estimates are adjusted for age, sex, glomerular filtration rate and proteinuria

TABLE 5

Baseline clinical and laboratory data of 177 patients who completed follow-up with further stratification into those without and with progression of kidney disease during the follow-up period

| | All patients (n = 177) | Non-progressors (n = 112) | Progressors (n = 65) |
|---|---|---|---|
| Gender (male/female), n (%) | 118/59 (67%/33%) | 74/38 (66%/34%) | 44/21 (68%/32%) |
| Age (years) | 46.4 ± 12.2 | 44.8 ± 12.6 | 49.1 ± 11.1$^a$ |
| Body mass index (kg/m$^2$) | 25.2 ± 3.7 | 24.8 ± 3.5 | 25.7 ± 3.9 |
| Current smokers, n (%) | 34 (19%) | 18 (16%) | 16 (25%) |
| Systolic blood pressure (mmHg) | 137 ± 20 | 136 ± 22 | 137 ± 17 |
| Diastolic blood pressure (mmHg) | 87 ± 13 | 86 ± 14 | 88 ± 12 |
| Blood pressure medication, n (%) | 143 (81%) | 82 (73%) | 61 (94%)$^c$ |
| Serum creatinine (mg/dL) | 2.15 ± 1.22 | 1.54 ± 0.61 | 3.21 ± 1.31$^d$ |
| Glomerular filtration rate (mL/min/1.73 m$^2$) | 64 ± 39 | 79 ± 38 | 38 ± 25$^d$ |
| | [35; 54; 89] | [50; 74; 99] | [20; 33; 46] |
| Proteinuria (g/24 h/1.73 m$^2$) | 1.01 ± 0.92 | 0.87 ± 0.95 | 1.25 ± 0.83$^d$ |
| | [0.20; 0.70; 1.63] | [0.14; 0.46; 1.25] | [0.61; 1.09; 1.78] |
| Serum albumin (g/dL) | 4.56 ± 0.40 | 4.57 ± 0.43 | 4.53 ± 0.36 |
| High-sens. C-reactive protein (mg/L) | 0.28 ± 0.31 | 0.28 ± 0.32 | 0.29 ± 0.31 |
| Adiponectin (μg/mL) | 6.31 ± 4.43 | 5.89 ± 4.27 | 7.05 ± 4.63$^a$ |
| | [3.43; 5.04; 7.73] | [2.93; 4.60; 7.34] | [4.10; 5.49; 8.61] |
| Metabolic syndrome, n (%)* | 85 (48%) | 47 (42%) | 38 (59%)$^a$ |
| Metabolic factors, n$^†$ | 2.43 ± 1.17 | 2.25 ± 1.21 | 2.74 ± 1.02$^c$ |
| Insulin (mU/L) | 13.50 ± 9.70 | 13.72 ± 11.14 | 13.11 ± 6.61 |
| HOMA-IR index | 3.46 ± 3.52 | 3.58 ± 4.15 | 3.25 ± 2.03 |
| Triglycerides (mg/dL) | 172 ± 95 | 159 ± 93 | 194 ± 96$^c$ |
| | [104; 144; 223] | [97; 131; 201] | [121; 181; 244] |

TABLE 5-continued

Baseline clinical and laboratory data of 177 patients who completed follow-up with further stratification into those without and with progression of kidney disease during the follow-up period

|  | All patients (n = 177) | Non-progressors (n = 112) | Progressors (n = 65) |
|---|---|---|---|
| HDL cholesterol (mg/dL) | 44 ± 15 | 46 ± 15 | 40 ± 13[b] |
| Glucose (mg/dL) | 98 ± 15 | 99 ± 16 | 97 ± 14 |
| Use of fibrates, n (%) | 9 (5%) | 6 (5%) | 3 (5%) |

Data are provided as mean ± SD [$25^{th}$, $50^{th}$, $75^{th}$ percentile where appropriate] or n (%)
[a] $p < 0.05$;
[b] $p < 0.01$;
[c] $p < 0.005$;
[d] $p < 0.001$ - comparison between progressors and non-progressors
*Definition according to the scientific statement from the American Heart Association (AHA) and the National Heart, Lung, and Blood Institute (NHLBI). Three of the following five parameters had to be present: elevated triglycerides ≧150 mg/dL (1.7 mmol/L) or on drug treatment for elevated triglycerides, reduced HDL-cholesterol <40 mg/dL (1.03 mmol/L) in men, <50 mg/dL (1.3 mmol/L) in women or on drug treatment for reduced HDL-cholesterol, hypertension: ≧130 mmHg systolic blood pressure or ≧85 mmHg diastolic blood pressure or on antihypertensive drug treatment in a patient with a history of hypertension, elevated fasting glucose: ≧100 mg/dL or on drug treatment for elevated glucose; since waist circumference was not available in our cohort we used BMI >30 kg/m$^2$.
†Metabolic factors: average number of factors considered in the definition of metabolic syndrome (see footnote above)

TABLE 6

The association of different variables with progression of kidney disease during the observation period using adjusted Cox Proportional Hazards regression models

| | Entire group | | | |
|---|---|---|---|---|
| | HR per unit increment (95% CI) | | | |
| Variable (increment) | adjusted for age and sex | P | adjusted for age, sex and the other 5 variables of this table | P |
| GFR (10 mL/min/1.73 m$^2$) | 0.67 (0.59-0.76) | <0.0001 | 0.64 (0.56-0.74) | <0.0001 |
| Proteinuria (1 g/24 h/1.73 m$^2$) | 1.30 (1.02-1.65) | 0.032 | 1.29 (0.98-1.70) | 0.065 |
| Adiponectin (1 µg/mL) | 1.08 (1.02-1.15) | 0.005 | 1.08 (1.02-1.15) | 0.013 |
| Metabolic syndrome (1 = yes, 0 = no) | 1.32 (0.77-2.27) | 0.32 | 1.77 (0.93-3.37) | 0.082 |
| Insulin (1 mU/L) | 0.98 (0.96-1.02) | 0.31 | 0.98 (0.86-1.13) | 0.81 |
| HOMA-IR index | 0.94 (0.85-1.04) | 0.26 | 0.91 (0.59-1.40) | 0.66 |

| | Stratified for Gender | | | |
|---|---|---|---|---|
| | Women | | Men | |
| | HR (95% CI) of disease progression per 1 µg/mL increment | | HR (95% CI) of disease progression per 1 µg/mL increment | |
| Adjusted for: | of adiponectin | P | of adiponectin | P |
| Age, GFR | 0.98 (0.83-1.16) | 0.83 | 1.16 (1.09-1.24) | <0.0001 |
| Age, GFR, proteinuria | 0.96 (0.81-1.13) | 0.61 | 1.16 (1.08-1.23) | <0.0001 |
| Age, GFR, proteinuria, insulin | 0.94 (0.80-1.12) | 0.49 | 1.15 (1.07-1.22) | <0.0001 |
| Age, GFR, proteinuria, HOMAR-IR | 0.93 (0.79-1.11) | 0.44 | 1.15 (1.08-1.22) | <0.0001 |
| Age, GFR, proteinuria, metabolic syndrome | 0.96 (0.82-1.13) | 0.62 | 1.16 (1.08-1.24) | <0.0001 |
| Age, GFR, proteinuria, NT-proBNP | 0.94 (0.80-1.11) | 0.47 | 1.15 (1.08-1.23) | <0.0001 |

The invention claimed is:

1. A method for the prediction of the progression of chronic kidney disease in a subject suspected to suffer from chronic kidney disease, said method comprising the step of determining the expression levels of at least one marker in a biological sample of the subject as compared to a standard or reference control, the marker being selected from the group consisting of
   (a) fibroblast growth factor 23 (FGF23); and
   (b) adiponectin
   wherein an elevated expression level of FGF23 and/or adiponectin as compared to the standard control or reference sample is indicative of the progression of said chronic kidney disease.

2. The method of claim 1, wherein said method comprises the determination of the expression level of said adiponectin in biological samples from male human subjects suspected to suffer from chronic kidney disease.

3. The method of claim 1, wherein said subject suspected to suffer from chronic kidney disease shows renal impairment or dysfunction.

4. The method of claim 1, wherein said subject suspected to suffer from chronic kidney disease suffer from a primary kidney disease.

5. The method of claim 4, wherein said primary kidney disease is a non-diabetic kidney disease.

6. The method of claim 4, wherein said primary kidney disease is selected from the group consisting of glomerulonephritis, adult polycystic kidney disease and interstitial nephritis.

7. The method of claim 1, wherein said standard control is or is derived from a biological sample of a healthy control individual or from healthy control individuals of the same species as the subject suspected to suffer from a chronic kidney disease.

8. The method of claim 1, wherein said determination of the expression levels of at least one marker selected from FGF23 and/or adiponectin comprises the detection of the FGF23 protein and/or the adiponectin protein in said biological sample or said biological samples.

9. The method of claim 1, wherein said biological sample is a tissue sample, a cell sample or a sample derived from a biological fluid.

10. The method of claim 9, wherein said biological fluid is selected from the group consisting of blood, feces, and urine.

11. The method of claim 10, wherein said blood is selected from whole blood, blood serum and blood plasma.

12. The method of claim 1, wherein said determination of the expression levels of at least one marker selected from FGF23 and adiponectin comprises a quantitative measurement of said marker or said markers.

13. The method of claim 12, wherein said quantitative measurement comprises an immunological assay or an immuno-detection assay.

14. The method of claim 12, wherein said assay is selected from ELISA, CIA, RIA, IRMA and Western-blot.

15. The method of claim 14, wherein said assay is an ELISA.

16. The method of claim 1, wherein an elevated level of at least 100 rU/ml of FGF23 protein is predictive for a fast progression of said chronic kidney disease.

17. The method of claim 1, wherein an elevated level of at least 3 μg/ml of adiponectin protein in human male subjects is predictive for a fast progression of said chronic kidney disease.

18. The method of claim 1, said method further comprising the measurement of further markers or of further physiological parameters.

19. The method of claim 18, wherein said measurement of further markers or of further physiological parameters comprises a determination of the glomerular filtration rate.

20. The method of claim 19, wherein the glomerular filtration rate is determined by use of the iohexol clearance technique or the iothalamate clearance technique.

21. The method of claim 19, wherein an elevation of the glomerular filtration rate is predictive for the progression of said chronic kidney disease.

22. The method of claim 21, wherein an elevated level of the glomerular filtration rate of at least 10 ml/min/1.73 m$^2$ is predictive for the progression of said chronic kidney disease.

23. The method of claim 18, wherein said measurement of further markers or of further physiological parameters comprises the determination of the expression level and/or protein level of apolipoprotein A-IV (ApoA-IV).

24. The method of claim 23, wherein an elevated ApoA-IV concentration of at least 3 mg/dl is predictive for the progression of said chronic kidney disease.

25. The method of claim 1, wherein the expression levels are determined using a detection molecule selected from the group consisting of an antibody, an antibody fragment, an antibody derivative, an aptamer.

26. The method of claim 25, wherein said detection molecule is an antibody for FGF-23.

27. The method of claim 25, wherein said detection molecule is an antibody for adiponectin.

* * * * *

SEQUENCE LISTING

```
<160> NUMBER OF SEQ ID NOS: 12

<210> SEQ ID NO 1
<211> LENGTH: 3018
<212> TYPE: DNA
<213> ORGANISM: homo sapiens
<220> FEATURE:
<221> NAME/KEY: CDS
<222> LOCATION: (147)..(902)
```

<400> SEQUENCE: 1

```
cggcaaaaag gagggaatcc agtctaggat cctcacacca gctacttgca agggagaagg      60
aaaaggccag taaggcctgg gccaggagag tcccgacagg agtgtcaggt ttcaatctca     120
gcaccagcca ctcagagcag ggcacg atg ttg ggg gcc cgc ctc agg ctc tgg      173
                              Met Leu Gly Ala Arg Leu Arg Leu Trp
                               1               5 gtc tgt gcc ttg tgc agc gtc tgc agc atg agc gtc ctc aga gcc tat      221
Val Cys Ala Leu Cys Ser Val Cys Ser Met Ser Val Leu Arg Ala Tyr
 10              15                  20                  25 ccc aat gcc tcc cca ctg ctc ggc tcc agc tgg ggt ggc ctg atc cac      269
Pro Asn Ala Ser Pro Leu Leu Gly Ser Ser Trp Gly Gly Leu Ile His
                 30                  35                  40 ctg tac aca gcc aca gcc agg aac agc tac cac ctg cag atc cac aag      317
Leu Tyr Thr Ala Thr Ala Arg Asn Ser Tyr His Leu Gln Ile His Lys
             45                  50                  55 aat ggc cat gtg gat ggc gca ccc cat cag acc atc tac agt gcc ctg      365
Asn Gly His Val Asp Gly Ala Pro His Gln Thr Ile Tyr Ser Ala Leu
         60                  65                  70 atg atc aga tca gag gat gct ggc ttt gtg gtg att aca ggt gtg atg      413
Met Ile Arg Ser Glu Asp Ala Gly Phe Val Val Ile Thr Gly Val Met
 75                  80                  85 agc aga aga tac ctc tgc atg gat ttc aga ggc aac att ttt gga tca      461
Ser Arg Arg Tyr Leu Cys Met Asp Phe Arg Gly Asn Ile Phe Gly Ser
 90                  95                 100                 105 cac tat ttc gac ccg gag aac tgc agg ttc caa cac cag acg ctg gaa      509
His Tyr Phe Asp Pro Glu Asn Cys Arg Phe Gln His Gln Thr Leu Glu
                110                 115                 120 aac ggg tac gac gtc tac cac tct cct cag tat cac ttc ctg gtc agt      557
Asn Gly Tyr Asp Val Tyr His Ser Pro Gln Tyr His Phe Leu Val Ser
            125                 130                 135 ctg ggc cgg gcg aag aga gcc ttc ctg cca ggc atg aac cca ccc ccg      605
Leu Gly Arg Ala Lys Arg Ala Phe Leu Pro Gly Met Asn Pro Pro Pro
        140                 145                 150 tac tcc cag ttc ctg tcc cgg agg aac gag atc ccc cta att cac ttc      653
Tyr Ser Gln Phe Leu Ser Arg Arg Asn Glu Ile Pro Leu Ile His Phe
    155                 160                 165 aac acc ccc ata cca cgg cgg cac acc cgg agc gcc gag gac gac tcg      701
Asn Thr Pro Ile Pro Arg Arg His Thr Arg Ser Ala Glu Asp Asp Ser
170                 175                 180                 185 gag cgg gac ccc ctg aac gtg ctg aag ccc cgg gcc cgg atg acc ccg      749
Glu Arg Asp Pro Leu Asn Val Leu Lys Pro Arg Ala Arg Met Thr Pro
                190                 195                 200 gcc ccg gcc tcc tgt tca cag gag ctc ccg agc gcc gag gac aac agc      797
Ala Pro Ala Ser Cys Ser Gln Glu Leu Pro Ser Ala Glu Asp Asn Ser
            205                 210                 215 ccg atg gcc agt gac cca tta ggg gtg gtc agg ggc ggt cga gtg aac      845
Pro Met Ala Ser Asp Pro Leu Gly Val Val Arg Gly Gly Arg Val Asn
        220                 225                 230 acg cac gct ggg gga acg ggc ccg gaa ggc tgc cgc ccc ttc gcc aag      893
Thr His Ala Gly Gly Thr Gly Pro Glu Gly Cys Arg Pro Phe Ala Lys
    235                 240                 245 ttc atc tag ggtcgctgga agggcaccct ctttaaccca tccctcagca              942
Phe Ile
250 aacgcagctc ttcccaagga ccaggtccct tgacgttccg aggatgggaa aggtgacagg    1002 ggcatgtatg gaatttgctg cttctctggg gtcccttcca caggaggtcc tgtgagaacc    1062 aacctttgag gcccaagtca tggggtttca ccgccttcct cactccatat agaacacctt    1122
```

```
tcccaataqg aaaccccaac aggtaaacta gaaatttccc cttcatgaag gtagagagaa    1182
ggggtctctc ccaacatatt tctcttcctt gtgcctctcc tctttatcac ttttaagcat    1242
aaaaaaaaaa aaaaaaaaaa aaaaaaaaaa aagcagtggg ttcctgagct caagactttg    1302
aaggtgtagg gaagaggaaa tcggagatcc cagaagcttc tccactgccc tatgcattta    1362
tgttagatgc cccgatccca ctggcatttg agtgtgcaaa ccttgacatt aacagctgaa    1422
tggggcaagt tgatgaaaac actactttca agccttcgtt cttccttgag catctctggg    1482
gaagagctgt caaagactg gtggtaggct ggtgaaaact tgacagctag acttgatgct    1542
tgctgaaatg aggcaggaat cataatagaa aactcagcct ccctacaggg tgagcacctt    1602
ctgtctcgct gtctccctct gtgcagccac agccagaggg cccagaatgg ccccactctg    1662
ttcccaagca gttcatgata cagcctcacc ttttggcccc atctctggtt tttgaaaatt    1722
tggtctaagg aataaatagc ttttacactg gctcacgaaa atctgccctg ctagaatttg    1782
cttttcaaaa tggaaataaa ttccaactct cctaagaggc atttaattaa ggctctactt    1842
ccaggttgag taggaatcca ttctgaacaa actacaaaaa tgtgactggg aaggggcctt    1902
tgagagactg ggactgctct gggttaggtt ttctgtggac tgaaaaatcg tgtccttttc    1962
tctaaatgaa gtggcatcaa ggactcaggg ggaaagaaat caggggacat gttatagaag    2022
ttatgaaaag acaaccacat ggtcaggctc ttgtctgtgg tctctagggc tctgcagcag    2082
cagtggctct tcgattagtt aaaactctcc taggctgaca catctgggtc tcaatcccct    2142
tggaaattct tggtgcatta aatgaagcct taccccatta ctgcggttct tcctgtaagg    2202
gggctccatt ttcctccctc tctttaaatg accacctaaa ggacagtata ttaacaagca    2262
aagtcgattc aacaacagct tcttcccagt cacttttttt tttctcactg ccatcacata    2322
ctaaccttat actttgatct attcttttg gttatgagag aaatgttggg caactgtttt    2382
tacctgatgt ttttaagctg aacttgaagg actggttcct attctgaaac agtaaaacta    2442
tgtataatag tatatagcca tgcatggcaa atattttaat atttctgttt tcatttcctg    2502
ttggaaatat tatcctgcat aatagctatt ggaggctcct cagtgaaaga tcccaaaagg    2562
attttggtgg aaaactagtt gtaatctcac aaactcaaca ctaccatcag gggttttctt    2622
tatggcaaag ccaaaatagc tcctacaatt tcttatatcc ctcgtcatgt ggcagtattt    2682
atttatttat ttggaagttt gcctatcctt ctatatttat agatatttat aaaaatgtaa    2742
cccctttttc ctttcttctg tttaaaataa aaataaaatt tatctcagct tctgttagct    2802
tatcctcttt gtagtactac ttaaaagcat gtcggaatat aagaataaaa aggattatgg    2862
gaggggaaca ttagggaaat ccagagaagg caaaattgaa aaaaagattt tagaatttta    2922
aaattttcaa agatttcttc cattcataag gagactcaat gattttaatt gatctagaca    2982 gaattatta agttttatca atattggatt tctggt                              3018
```

<210> SEQ ID NO 2
<211> LENGTH: 251
<212> TYPE: PRT
<213> ORGANISM: homo sapiens

<400> SEQUENCE: 2

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg

```
                      35                  40                  45
Asn Ser Tyr His Leu Gln Ile His Lys Asn Gly His Val Asp Gly Ala
 50                  55                  60

Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                     85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
                115                 120                 125

Ser Pro Gln Tyr His Phe Leu Val Ser Leu Gly Arg Ala Lys Arg Ala
            130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 3
<211> LENGTH: 528
<212> TYPE: DNA
<213> ORGANISM: felis catus
<220> FEATURE:
<221> NAME/KEY: CDS
<222> LOCATION: (1)..(528)

<400> SEQUENCE: 3 atg tca ggg acc cgc ctt ggg ctc ctg gtc tct gtc ctg tgc tgg gta      48
Met Ser Gly Thr Arg Leu Gly Leu Leu Val Ser Val Leu Cys Trp Val
  1               5                  10                  15 gtc aga gcc tat cct aac acc tcc ccg ctg ctg ggc tcc agc tgg ggt      96
Val Arg Ala Tyr Pro Asn Thr Ser Pro Leu Leu Gly Ser Ser Trp Gly
             20                  25                  30 ggc ctg acc cac ctg tac acg gcc aca gcc agg aac agc tac cac ctg     144
Gly Leu Thr His Leu Tyr Thr Ala Thr Ala Arg Asn Ser Tyr His Leu
         35                  40                  45 cag ata cac aag gac ggc cat gtg gat ggc aca ccc cat cag acc atc     192
Gln Ile His Lys Asp Gly His Val Asp Gly Thr Pro His Gln Thr Ile
     50                  55                  60 tac agt gcc ctg atg atc aga tcg gag gat gcc ggc ttt gtg gtg ata     240
Tyr Ser Ala Leu Met Ile Arg Ser Glu Asp Ala Gly Phe Val Val Ile
 65                  70                  75                  80 aca ggt gtg atg agt cag agg tac ctc tgt atg gac ttc aga ggc aat     288
Thr Gly Val Met Ser Gln Arg Tyr Leu Cys Met Asp Phe Arg Gly Asn
                 85                  90                  95 atc ttc gga tcg cac ctc ttc agc ccc gag agc tgc agg ttc cga cag     336
Ile Phe Gly Ser His Leu Phe Ser Pro Glu Ser Cys Arg Phe Arg Gln
            100                 105                 110
```

```
cgg acg ctg gaa aac ggc tac gac gtg tac cac tcc ccg cag cac cgc         384
Arg Thr Leu Glu Asn Gly Tyr Asp Val Tyr His Ser Pro Gln His Arg
        115                 120                 125 ttc cta gtc agc ctg ggc ccg gcc aag agg gcc ctc ctg ccg ggc acc         432
Phe Leu Val Ser Leu Gly Pro Ala Lys Arg Ala Leu Leu Pro Gly Thr
130                 135                 140 aac cct ccg cct tac tcc cag ttc ctg tcg cgg agg aac gag atc ccc         480
Asn Pro Pro Pro Tyr Ser Gln Phe Leu Ser Arg Arg Asn Glu Ile Pro
145                 150                 155                 160 ctc gtc cac ttt aac acc ccg cgg ccg cgg cgc cac acc cgc aac gcc         528
Leu Val His Phe Asn Thr Pro Arg Pro Arg Arg His Thr Arg Asn Ala
                165                 170                 175

<210> SEQ ID NO 4
<211> LENGTH: 176
<212> TYPE: PRT
<213> ORGANISM: felis catus

<400> SEQUENCE: 4

Met Ser Gly Thr Arg Leu Gly Leu Leu Val Ser Val Leu Cys Trp Val
1               5                   10                  15

Val Arg Ala Tyr Pro Asn Thr Ser Pro Leu Leu Gly Ser Ser Trp Gly
            20                  25                  30

Gly Leu Thr His Leu Tyr Thr Ala Thr Ala Arg Asn Ser Tyr His Leu
        35                  40                  45

Gln Ile His Lys Asp Gly His Val Asp Gly Thr Pro His Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Gln Arg Tyr Leu Cys Met Asp Phe Arg Gly Asn
                85                  90                  95

Ile Phe Gly Ser His Leu Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Pro Ala Lys Arg Ala Leu Leu Pro Gly Thr
    130                 135                 140

Asn Pro Pro Pro Tyr Ser Gln Phe Leu Ser Arg Arg Asn Glu Ile Pro
145                 150                 155                 160

Leu Val His Phe Asn Thr Pro Arg Pro Arg Arg His Thr Arg Asn Ala
                165                 170                 175

<210> SEQ ID NO 5
<211> LENGTH: 738
<212> TYPE: DNA
<213> ORGANISM: Canis familiaris
<220> FEATURE:
<221> NAME/KEY: CDS
<222> LOCATION: (1)..(738)

<400> SEQUENCE: 5 atg tct ggc acc cgc ctt gga ttc ctg gtc tct gtc ctg tgc tgg gta         48
Met Ser Gly Thr Arg Leu Gly Phe Leu Val Ser Val Leu Cys Trp Val
1               5                   10                  15 gtc aga gcc tat tcc aac acc tcc ccg ctg ctc ggc tcc agc tgg ggt         96
Val Arg Ala Tyr Ser Asn Thr Ser Pro Leu Leu Gly Ser Ser Trp Gly
            20                  25                  30 agc cta acc cac ctg tat acg gcc aca gcc agg aac agc tac cac ctg        144
Ser Leu Thr His Leu Tyr Thr Ala Thr Ala Arg Asn Ser Tyr His Leu
        35                  40                  45
```

```
cag atc cac aag gac ggc cat gtg gat ggc aca cct cat cag acc atc    192
Gln Ile His Lys Asp Gly His Val Asp Gly Thr Pro His Gln Thr Ile
 50                  55                  60 tac agt gcc ttg atg atc cgg tca gag gat gcc ggc ttt gtg gtg ata    240
Tyr Ser Ala Leu Met Ile Arg Ser Glu Asp Ala Gly Phe Val Val Ile
 65                  70                  75                  80 aca ggt gtg atg agt agg agg tac ctc tgt atg gac ttc aga ggc aac    288
Thr Gly Val Met Ser Arg Arg Tyr Leu Cys Met Asp Phe Arg Gly Asn
                 85                  90                  95 atc ttt gga tca cac ctc ttc agc ccg gag agc tgc cgg ttc cga cag    336
Ile Phe Gly Ser His Leu Phe Ser Pro Glu Ser Cys Arg Phe Arg Gln
            100                 105                 110 cgg acg ctg gag aac ggc tac gac gtg tac cac tcc ccg cag cac cgc    384
Arg Thr Leu Glu Asn Gly Tyr Asp Val Tyr His Ser Pro Gln His Arg
        115                 120                 125 ttc ctc gtc agc ctg ggc cag gcc aag agg gcc ttc ctg ccc ggc acc    432
Phe Leu Val Ser Leu Gly Gln Ala Lys Arg Ala Phe Leu Pro Gly Thr
    130                 135                 140 aac ccg ccg ccc tac tcg cag ttc ctg tcc cgg agg aac gag atc ccc    480
Asn Pro Pro Pro Tyr Ser Gln Phe Leu Ser Arg Arg Asn Glu Ile Pro
145                 150                 155                 160 ctc gtg cac ttc cac acg ccc agg ccg cgg cgg cac acg cgc agc gcc    528
Leu Val His Phe His Thr Pro Arg Pro Arg Arg His Thr Arg Ser Ala
                165                 170                 175 gag gcc ccg gag cgc gac ccg ctg aac gtg ctg aag ccc agg ccg cgc    576
Glu Ala Pro Glu Arg Asp Pro Leu Asn Val Leu Lys Pro Arg Pro Arg
            180                 185                 190 ttg gcc ccc gcc ccg gcc tcc tgc tcg cag gag ctc ccg agc gcc gag    624
Leu Ala Pro Ala Pro Ala Ser Cys Ser Gln Glu Leu Pro Ser Ala Glu
        195                 200                 205 gac ccc ggc gcc ccg gcc agc gac ccg ctc ggg gtg ctc agg ggc cac    672
Asp Pro Gly Ala Pro Ala Ser Asp Pro Leu Gly Val Leu Arg Gly His
    210                 215                 220 agg gcc aac gcg cgc gcc ggc ggg gtg ggc gtg gac agg tgc cgc gcc    720
Arg Ala Asn Ala Arg Ala Gly Gly Val Gly Val Asp Arg Cys Arg Ala
225                 230                 235                 240 ttc ccc acg ccc atc tag                                            738
Phe Pro Thr Pro Ile
                245

<210> SEQ ID NO 6
<211> LENGTH: 245
<212> TYPE: PRT
<213> ORGANISM: Canis familiaris

<400> SEQUENCE: 6

Met Ser Gly Thr Arg Leu Gly Phe Leu Val Ser Val Leu Cys Trp Val
 1               5                  10                  15

Val Arg Ala Tyr Ser Asn Thr Ser Pro Leu Leu Gly Ser Ser Trp Gly
                20                  25                  30

Ser Leu Thr His Leu Tyr Thr Ala Thr Ala Arg Asn Ser Tyr His Leu
            35                  40                  45

Gln Ile His Lys Asp Gly His Val Asp Gly Thr Pro His Gln Thr Ile
        50                  55                  60

Tyr Ser Ala Leu Met Ile Arg Ser Glu Asp Ala Gly Phe Val Val Ile
 65                  70                  75                  80

Thr Gly Val Met Ser Arg Arg Tyr Leu Cys Met Asp Phe Arg Gly Asn
                 85                  90                  95

Ile Phe Gly Ser His Leu Phe Ser Pro Glu Ser Cys Arg Phe Arg Gln
            100                 105                 110
```

```
Arg Thr Leu Glu Asn Gly Tyr Asp Val Tyr His Ser Pro Gln His Arg
        115                 120                 125
Phe Leu Val Ser Leu Gly Gln Ala Lys Arg Ala Phe Leu Pro Gly Thr
    130                 135                 140
Asn Pro Pro Tyr Ser Gln Phe Leu Ser Arg Asn Glu Ile Pro
145                 150                 155                 160
Leu Val His Phe His Thr Pro Arg Pro Arg His Thr Arg Ser Ala
                165                 170                 175
Glu Ala Pro Glu Arg Asp Pro Leu Asn Val Leu Lys Pro Arg Pro Arg
            180                 185                 190
Leu Ala Pro Ala Pro Ala Ser Cys Ser Gln Glu Leu Pro Ser Ala Glu
        195                 200                 205
Asp Pro Gly Ala Pro Ala Ser Asp Pro Leu Gly Val Leu Arg Gly His
    210                 215                 220
Arg Ala Asn Ala Arg Ala Gly Gly Val Gly Val Asp Arg Cys Arg Ala
225                 230                 235                 240
Phe Pro Thr Pro Ile
                245

<210> SEQ ID NO 7
<211> LENGTH: 4576
<212> TYPE: DNA
<213> ORGANISM: Homo sapiens
<220> FEATURE:
<221> NAME/KEY: CDS
<222> LOCATION: (85)..(819)

<400> SEQUENCE: 7
aggctgttga ggctgggcca tctcctcctc acttccattc tgactgcagt ctgtggttct      60
gattccatac cagagggggct cagg atg ctg ttg ctg gga gct gtt cta ctg      111
                            Met Leu Leu Leu Gly Ala Val Leu Leu
                              1               5 cta tta gct ctg ccc ggt cat gac cag gaa acc acg act caa ggg ccc      159
Leu Leu Ala Leu Pro Gly His Asp Gln Glu Thr Thr Thr Gln Gly Pro
 10              15                  20                  25 gga gtc ctg ctt ccc ctg ccc aag ggg gcc tgc aca ggt tgg atg gcg      207
Gly Val Leu Leu Pro Leu Pro Lys Gly Ala Cys Thr Gly Trp Met Ala
             30                  35                  40 ggc atc cca ggg cat ccg ggc cat aat ggg gcc cca ggc cgt gat ggc      255
Gly Ile Pro Gly His Pro Gly His Asn Gly Ala Pro Gly Arg Asp Gly
         45                  50                  55 aga gat ggc acc cct ggt gag aag ggt gag aaa gga gat cca ggt ctt      303
Arg Asp Gly Thr Pro Gly Glu Lys Gly Glu Lys Gly Asp Pro Gly Leu
     60                  65                  70 att ggt cct aag gga gac atc ggt gaa acc gga gta ccc ggg gct gaa      351
Ile Gly Pro Lys Gly Asp Ile Gly Glu Thr Gly Val Pro Gly Ala Glu
 75                  80                  85 ggt ccc cga ggc ttt ccg gga atc caa ggc agg aaa gga gaa cct gga      399
Gly Pro Arg Gly Phe Pro Gly Ile Gln Gly Arg Lys Gly Glu Pro Gly
             90                  95                 100                 105 gaa ggt gcc tat gta tac cgc tca gca ttc agt gtg gga ttg gag act      447
Glu Gly Ala Tyr Val Tyr Arg Ser Ala Phe Ser Val Gly Leu Glu Thr
                110                 115                 120 tac gtt act atc ccc aac atg ccc att cgc ttt acc aag atc ttc tac      495
Tyr Val Thr Ile Pro Asn Met Pro Ile Arg Phe Thr Lys Ile Phe Tyr
            125                 130                 135 aat cag caa aac cac tat gat ggc tcc act ggt aaa ttc cac tgc aac      543
Asn Gln Gln Asn His Tyr Asp Gly Ser Thr Gly Lys Phe His Cys Asn
        140                 145                 150
```

```
att cct ggg ctg tac tac ttt gcc tac cac atc aca gtc tat atg aag      591
Ile Pro Gly Leu Tyr Tyr Phe Ala Tyr His Ile Thr Val Tyr Met Lys
    155                 160                 165 gat gtg aag gtc agc ctc ttc aag aag gac aag gct atg ctc ttc acc      639
Asp Val Lys Val Ser Leu Phe Lys Lys Asp Lys Ala Met Leu Phe Thr
170                 175                 180                 185 tat gat cag tac cag gaa aat aat gtg gac cag gcc tcc ggc tct gtg      687
Tyr Asp Gln Tyr Gln Glu Asn Asn Val Asp Gln Ala Ser Gly Ser Val
                190                 195                 200 ctc ctg cat ctg gag gtg ggc gac caa gtc tgg ctc cag gtg tat ggg      735
Leu Leu His Leu Glu Val Gly Asp Gln Val Trp Leu Gln Val Tyr Gly
            205                 210                 215 gaa gga gag cgt aat gga ctc tat gct gat aat gac aat gac tcc acc      783
Glu Gly Glu Arg Asn Gly Leu Tyr Ala Asp Asn Asp Asn Asp Ser Thr
        220                 225                 230 ttc aca ggc ttt ctt ctc tac cat gac acc aac tga tcaccactaa           829
Phe Thr Gly Phe Leu Leu Tyr His Asp Thr Asn
    235                 240 ctcagagcct cctccaggcc aaacagcccc aaagtcaatt aaaggctttc agtacggtta     889
ggaagttgat tattatttag ttggaggcct ttagatatta ttcattcatt tactcattca     949
tttattcatt cattcatcga gtaactttaa aaaaatcata tgctatgttc ccagtcctgg    1009
ggagcttcac aaacatgacc agataactga ctagaaagaa gtagttgaca gtgctatttt    1069
gtgcccactg tctctcctga tgctcatatc aatcctataa ggcacaggga caagcattc    1129
tcctgttttt acagattgta tcctgaggct gagagagtta agtgaatgtc taaggtcaca    1189
cagtattaag tgacagtgct agaaatcaaa cccagagctg tggactttgt tcactagact    1249
gtgccctttt atagaggtac atgttctctt tggagtgttg gtaggtgtct gtttcccacc    1309
tcacctgaga gccattgaat ttgccttcct catgaattaa aacctccccc aagcagagct    1369
tcctcagaga aagtggttct atgatgacgt cctgtcttgg aaggactact actcaatggc    1429
ccctgcacta ctctacttcc tcttacctat gtcccttctc atgcctttcc ctccaacggg    1489
gaaagccaac tccatctcta agtgccgaac tcatccctgt tcctcaaggc cacctggcca    1549
ggagcttctc tgatgtgata tccactttt ttttttttga gatggagtct cactctgtca    1609
cccaggctgg agtacagtga cacgacctcg gctcactgca gcctccttct cctgggtcca    1669
agcaattatt gtgcctcagc ctcccgagta gctgagactt caggtgcatt ccaccacaca    1729
tggctaattt ttgtattttt agtagaaatg gggtttcgtc atgttggcca ggctggtctc    1789
gaactcctgg cctaggtgat ccacccgcct cgacctccca aagtgctggg attacaggca    1849
tgagccacca tgcccagtcg atatctcact ttttattttg ccatggatga gagtcctggg    1909
tgtgaggaac acctcccacc aggctagagg caactgccca ggaaggactg tgcttccgtc    1969
acctctaaat cccttgcaga tccttgataa atgcctcatg aagaccaatc tcttgaatcc    2029
catatctacc cagaattaac tccattccag tctctgcatg taatcagttt tatccacaga    2089
aacattttca ttttaggaaa tccctggttt taagtatcaa tccttgttca gctggacaat    2149
atgaatcttt tccactgaag ttagggatga ctgtgatttt cagaacacgt ccagaatttt    2209
tcatcaagaa ggtagcttga gcctgaaatg caaaacccat ggaggaattc tgaagccatt    2269
gtctccttga gtaccaacag ggtcagggaa gactgggcct cctgaattta ttattgttct    2329
ttaagaatta caggttgagg tagttgatgg tggtaaacat tctctcagga gacaataact    2389
ccagtgatgt tcttcaaaga tttagcaaa aacagagtaa atagcattct ctatcaatat    2449
ataaatttaa aaaactatct ttttgcttac agttttaaat tctgaacaat tctctcttat    2509
```

```
atgtgtattg ctaatcatta aggtattatt ttttccacat ataaagcttt gtcttttgt      2569 tgttgttgtt gttttttaaga tggagtttcc ctctgttgcc aggctagagt gcagtggcat    2629
gatctcggct tactgcaacc tttgcctccc aggttcaagc gattcttctg cctcagcctc     2689
ccgagtagct gggaccacag gtgcctacca ccatgccagg ctaatttttg tatttttagt     2749
aaagacaggg tttcaccata ttggccaggc tggtctcgaa ctcctgacct tgtgatctgc     2809
ccgcctccat ttttgttgtt attttttgag aaagatagat atgaggttta gagagggatg     2869
aagaggtgag agtaagcctt gtgttagtca gaactctgtg ttgtgaatgt cattcacaac     2929
agaaaaccca aaatattatg caaactactg taagcaagaa aaataaagga aaaatggaaa    2989
catttattcc tttgcataat agaaattacc agagttgttc tgtctttaga taaggtttga    3049
accaaagctc aaaacaatca agaccctttt ctgtatgtcc ttctgttctg ccttccgcag    3109
tgtaggcttt accctcaggt gctacacagt atagttctag ggtttccctc ccgatatcaa    3169
aaagactgtg gcctgcccag ctctcgtatc cccaagccac accatctggc taaatggaca    3229
tcatgttttc tggtgatgcc aaagaggag agaggaagct ctctttccca gatgccccag     3289
caagtgtaac cttgcatctc attgctctgg ctgagttgtg tgcctgtttc tgaccaatca    3349
ctgagtcagg aggatgaaat attcatattg acttaattgc agcttaagtt aggggtatgt    3409
agaggtattt tccctaaagc aaaattggga cactgttatc agaaatagga gagtggatga    3469
tagatgcaaa ataatacctg tccacaacaa actcttaatg ctgtgtttga gctttcatga    3529
gtttcccaga gagacatagc tggaaaattc ctattgattt tctctaaaat ttcaacaagt    3589
agctaaagtc tggctatgct cacagtctca catctggttg gggtgggctc cttacagaac    3649
acgctttcac agttacccta aactctctgg ggcagggtta ttcctttgtg gaaccagagg    3709
cacagagaga gtcaactgag gccaaaagag gcctgagaga aactgaggtc aagatttcag    3769
gattaatggt cctgtgatgc tttgaagtac aattgtggat ttgtccaatt ctctttagtt    3829
ctgtcagctt ttgcttcata tattttagcg ctctattatt agatatatac atgtttagta    3889
ttatgtctta ttggtgcatt tactctctta tcattatgta atgtccttct ttatctgtga    3949 taatttttctg tgttctgaag tctactttgt ctaaaaataa catacgcact caacttcctt    4009
ttctttcttc cttcctttct ttcttccttc ctttctttct ctctctctct ctttccttcc    4069
ttccttcctc cttttctttc tctctctctc tctctctctt tttttgacag actctcgttc    4129
tgtggccctg gctggagttc agtggtgtga tcttggctca ctgctacctc taccatgagc    4189
aattctcctg cctcagcctc ccaagtagct ggaactacag gctcatgcca ctgcgcccag    4249 ctaattttg tatttttcgt agagacgggg tttcaccaca ttcgtcaggt tggtttcaaa     4309
ctcctgactt tgtgatccac ccgcctcggc ctcccaaagt gctgggatta caggcatgag    4369
ccatcacacc tggtcaactt tcttttgatt agtgttttg tggtatatct ttttccatca     4429
tgttacttta aatatatcta tattattgta tttaaaatgt gtttcttaca gactgcatgt    4489
agttgggtat aattttttatc cagtctaaaa atatctgtct tttaattggt gtttagacaa   4549
tttatattta ataaaattgt tgaattt                                         4576
```

<210> SEQ ID NO 8
<211> LENGTH: 244
<212> TYPE: PRT
<213> ORGANISM: Homo sapiens

<400> SEQUENCE: 8

Met Leu Leu Leu Gly Ala Val Leu Leu Leu Leu Ala Leu Pro Gly His

|   | 1 |   |   |   | 5 |   |   |   |   | 10 |   |   |   |   | 15 |
|---|---|---|---|---|---|---|---|---|---|---|---|---|---|---|---|

Asp Gln Glu Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
 50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                    85                  90                  95

Ile Gln Gly Arg Lys Gly Glu Pro Gly Glu Gly Ala Tyr Val Tyr Arg
                100                 105                 110

Ser Ala Phe Ser Val Gly Leu Glu Thr Tyr Val Thr Ile Pro Asn Met
                115                 120                 125

Pro Ile Arg Phe Thr Lys Ile Phe Tyr Asn Gln Gln Asn His Tyr Asp
            130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
                180                 185                 190

Asn Val Asp Gln Ala Ser Gly Ser Val Leu Leu His Leu Glu Val Gly
            195                 200                 205

Asp Gln Val Trp Leu Gln Val Tyr Gly Glu Gly Glu Arg Asn Gly Leu
            210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 9
<211> LENGTH: 735
<212> TYPE: DNA
<213> ORGANISM: Felis catus
<220> FEATURE:
<221> NAME/KEY: CDS
<222> LOCATION: (1)..(735)

<400> SEQUENCE: 9

| atg | ctg | ttg | cta | cga | gct | gtt | cta | ttg | cta | ctg | gtc | ctg | ccc | att | cgt |  48 |
|---|---|---|---|---|---|---|---|---|---|---|---|---|---|---|---|---|
| Met | Leu | Leu | Leu | Arg | Ala | Val | Leu | Leu | Leu | Leu | Val | Leu | Pro | Ile | Arg | |
| 1 | | | | 5 | | | | | 10 | | | | | 15 | | |

| ggc | cag | gac | tcc | gag | aca | gaa | ggg | cct | gga | gtc | gtt | gtt | ccc | ctg | cca |  96 |
|---|---|---|---|---|---|---|---|---|---|---|---|---|---|---|---|---|
| Gly | Gln | Asp | Ser | Glu | Thr | Glu | Gly | Pro | Gly | Val | Val | Val | Pro | Leu | Pro | |
| | | | 20 | | | | | 25 | | | | | 30 | | | |

| aaa | ggg | gcc | tgc | aca | ggt | tgg | atg | gca | ggc | att | cca | ggg | cat | ccc | ggc | 144 |
|---|---|---|---|---|---|---|---|---|---|---|---|---|---|---|---|---|
| Lys | Gly | Ala | Cys | Thr | Gly | Trp | Met | Ala | Gly | Ile | Pro | Gly | His | Pro | Gly | |
| | | | 35 | | | | | 40 | | | | | 45 | | | |

| cac | aat | ggg | acc | cca | ggc | cgg | gat | ggt | aga | gat | ggc | acc | ccg | ggt | gaa | 192 |
|---|---|---|---|---|---|---|---|---|---|---|---|---|---|---|---|---|
| His | Asn | Gly | Thr | Pro | Gly | Arg | Asp | Gly | Arg | Asp | Gly | Thr | Pro | Gly | Glu | |
| | 50 | | | | | 55 | | | | | 60 | | | | | |

| aag | ggt | gag | aaa | gga | gat | cca | ggt | ctt | gtt | ggt | cct | aag | ggt | gac | act | 240 |
|---|---|---|---|---|---|---|---|---|---|---|---|---|---|---|---|---|
| Lys | Gly | Glu | Lys | Gly | Asp | Pro | Gly | Leu | Val | Gly | Pro | Lys | Gly | Asp | Thr | |
| 65 | | | | | 70 | | | | | 75 | | | | | 80 | |

| ggt | gaa | act | gga | gta | act | ggg | att | gaa | ggt | ccc | aga | ggt | ttt | tca | aga | 288 |
|---|---|---|---|---|---|---|---|---|---|---|---|---|---|---|---|---|
| Gly | Glu | Thr | Gly | Val | Thr | Gly | Ile | Glu | Gly | Pro | Arg | Gly | Phe | Ser | Arg | |
| | | | | 85 | | | | | 90 | | | | | 95 | | |

```
att cca ggc agg aaa aga gaa cct gga gaa agt gcc tac gta tac cgc        336
Ile Pro Gly Arg Lys Arg Glu Pro Gly Glu Ser Ala Tyr Val Tyr Arg
        100                 105                 110 tca gcg ttc agt gtg gga ttg gag agt cgg gtc aca gtc ccc aat gtt        384
Ser Ala Phe Ser Val Gly Leu Glu Ser Arg Val Thr Val Pro Asn Val
            115                 120                 125 ccc att cgc ttt acc aaa atc ttc tac aat cag caa aac cac tac gat        432
Pro Ile Arg Phe Thr Lys Ile Phe Tyr Asn Gln Gln Asn His Tyr Asp
130                 135                 140 gtt acc act gga aaa ttc cac tgc aac att ccc ggg cta tac tac ttc        480
Val Thr Thr Gly Lys Phe His Cys Asn Ile Pro Gly Leu Tyr Tyr Phe
145                 150                 155                 160 tcc tac cac atc aca gtc tac ttg aag gac gtc aag gtc agt ctc tac        528
Ser Tyr His Ile Thr Val Tyr Leu Lys Asp Val Lys Val Ser Leu Tyr
                165                 170                 175 aag aga gac aag gcg atg ctc ttc acc tac gac cag tac cag gag aag        576
Lys Arg Asp Lys Ala Met Leu Phe Thr Tyr Asp Gln Tyr Gln Glu Lys
            180                 185                 190 aat gtg gac cag gcc tct ggc tct gtg ctc ctc cat ctg gag acg ggc        624
Asn Val Asp Gln Ala Ser Gly Ser Val Leu Leu His Leu Glu Thr Gly
        195                 200                 205 gat gaa gtc tgg ctc cag gtg tat ggg gat ggg gac tat aat ggg ctc        672
Asp Glu Val Trp Leu Gln Val Tyr Gly Asp Gly Asp Tyr Asn Gly Leu
210                 215                 220 tat gca gat aac gtc aat gac tcc acc ttt aca ggc ttc ctt ctc tac        720
Tyr Ala Asp Asn Val Asn Asp Ser Thr Phe Thr Gly Phe Leu Leu Tyr
225                 230                 235                 240 tat gac acc gtt tga                                                    735
Tyr Asp Thr Val <210> SEQ ID NO 10
<211> LENGTH: 244
<212> TYPE: PRT
<213> ORGANISM: Felis catus

<400> SEQUENCE: 10

Met Leu Leu Leu Arg Ala Val Leu Leu Leu Val Leu Pro Ile Arg
1               5                   10                  15

Gly Gln Asp Ser Glu Thr Glu Gly Pro Gly Val Val Pro Leu Pro
            20                  25                  30

Lys Gly Ala Cys Thr Gly Trp Met Ala Gly Ile Pro Gly His Pro Gly
        35                  40                  45

His Asn Gly Thr Pro Gly Arg Asp Gly Arg Asp Gly Thr Pro Gly Glu
    50                  55                  60

Lys Gly Glu Lys Gly Asp Pro Gly Leu Val Gly Pro Lys Gly Asp Thr
65                  70                  75                  80

Gly Glu Thr Gly Val Thr Gly Ile Glu Gly Pro Arg Gly Phe Ser Arg
                85                  90                  95

Ile Pro Gly Arg Lys Arg Glu Pro Gly Glu Ser Ala Tyr Val Tyr Arg
            100                 105                 110

Ser Ala Phe Ser Val Gly Leu Glu Ser Arg Val Thr Val Pro Asn Val
        115                 120                 125

Pro Ile Arg Phe Thr Lys Ile Phe Tyr Asn Gln Gln Asn His Tyr Asp
    130                 135                 140

Val Thr Thr Gly Lys Phe His Cys Asn Ile Pro Gly Leu Tyr Tyr Phe
145                 150                 155                 160

Ser Tyr His Ile Thr Val Tyr Leu Lys Asp Val Lys Val Ser Leu Tyr
                165                 170                 175
```

```
Lys Arg Asp Lys Ala Met Leu Phe Thr Tyr Asp Gln Tyr Gln Glu Lys
            180                 185                 190

Asn Val Asp Gln Ala Ser Gly Ser Val Leu Leu His Leu Glu Thr Gly
        195                 200                 205

Asp Glu Val Trp Leu Gln Val Tyr Gly Asp Gly Asp Tyr Asn Gly Leu
    210                 215                 220

Tyr Ala Asp Asn Val Asn Asp Ser Thr Phe Thr Gly Phe Leu Leu Tyr
225                 230                 235                 240

Tyr Asp Thr Val

<210> SEQ ID NO 11
<211> LENGTH: 763
<212> TYPE: DNA
<213> ORGANISM: Canis familiaris
<220> FEATURE:
<221> NAME/KEY: CDS
<222> LOCATION: (29)..(763)

<400> SEQUENCE: 11
gtctgattct acacctgagg ggctcagg atg ctg ttg cta cga gct gtt cta          52
                                Met Leu Leu Leu Arg Ala Val Leu
                                 1               5 ctg cta cta gtc ctg ccc gct cac ggc cag gac tcc gtg gca gaa ggg        100
Leu Leu Leu Val Leu Pro Ala His Gly Gln Asp Ser Val Ala Glu Gly
     10                  15                  20 cct gga gtc ctg ctt ccc ctg ccg aag ggg gcc tgc cca ggt tgg atg        148
Pro Gly Val Leu Leu Pro Leu Pro Lys Gly Ala Cys Pro Gly Trp Met
 25                  30                  35                  40 gca ggc atc cca ggg cat cct ggc cac aat ggg acc cca ggc cgt gat        196
Ala Gly Ile Pro Gly His Pro Gly His Asn Gly Thr Pro Gly Arg Asp
                 45                  50                  55 ggc aga gat ggc acc cct ggt gaa aag ggt gag aaa gga gat cca ggt        244
Gly Arg Asp Gly Thr Pro Gly Glu Lys Gly Glu Lys Gly Asp Pro Gly
         60                  65                  70 ctt gtt ggt cct aag ggt gac act ggt gaa act gga gta act ggg gtt        292
Leu Val Gly Pro Lys Gly Asp Thr Gly Glu Thr Gly Val Thr Gly Val
     75                  80                  85 gaa ggt ccc cga ggc ttt cca gga acc cca gga agg aaa gga gaa cct        340
Glu Gly Pro Arg Gly Phe Pro Gly Thr Pro Gly Arg Lys Gly Glu Pro
 90                  95                 100 ggg gaa agt gcc tat gta cac cgt tcg gca ttc agt gtg ggg ttg gag        388
Gly Glu Ser Ala Tyr Val His Arg Ser Ala Phe Ser Val Gly Leu Glu
105                 110                 115                 120 agc cgg atc act gtc ccc aat gtt ccc att cgc ttt acc aaa atc ttc        436
Ser Arg Ile Thr Val Pro Asn Val Pro Ile Arg Phe Thr Lys Ile Phe
                125                 130                 135 tac aat ctg caa aac cac tac gat ggc acc act gga aaa ttt cac tgc        484
Tyr Asn Leu Gln Asn His Tyr Asp Gly Thr Thr Gly Lys Phe His Cys
        140                 145                 150 aac att cct ggg ctg tac tac ttc tcc tac cac atc aca gtc tac ttg        532
Asn Ile Pro Gly Leu Tyr Tyr Phe Ser Tyr His Ile Thr Val Tyr Leu
    155                 160                 165 aag gat gtc aag gtc agc ctc tac aag aaa gac aag gct atg ctc ttc        580
Lys Asp Val Lys Val Ser Leu Tyr Lys Lys Asp Lys Ala Met Leu Phe
170                 175                 180 acc tat gac cag tac cag gag aag aac gtg gac cag gcc tct ggc tct        628
Thr Tyr Asp Gln Tyr Gln Glu Lys Asn Val Asp Gln Ala Ser Gly Ser
185                 190                 195                 200
```

```
gtg ctc ctt cat ctg gaa gtg ggc gac caa gtc tgg ctc cag gtg tac      676
Val Leu Leu His Leu Glu Val Gly Asp Gln Val Trp Leu Gln Val Tyr
            205                 210                 215 ggg gat ggg gac tcc tat ggg atc tac gca gat aac gtc aat gac tcc      724
Gly Asp Gly Asp Ser Tyr Gly Ile Tyr Ala Asp Asn Val Asn Asp Ser
        220                 225                 230 acc ttt acg ggc ttc ctt ctc tac cat gac acc aac tga                  763
Thr Phe Thr Gly Phe Leu Leu Tyr His Asp Thr Asn
        235                 240

<210> SEQ ID NO 12
<211> LENGTH: 244
<212> TYPE: PRT
<213> ORGANISM: Canis familiaris

<400> SEQUENCE: 12

Met Leu Leu Leu Arg Ala Val Leu Leu Leu Val Leu Pro Ala His
1               5                   10                  15

Gly Gln Asp Ser Val Ala Glu Gly Pro Gly Val Leu Leu Pro Leu Pro
                20                  25                  30

Lys Gly Ala Cys Pro Gly Trp Met Ala Gly Ile Pro Gly His Pro Gly
            35                  40                  45

His Asn Gly Thr Pro Gly Arg Asp Gly Arg Asp Gly Thr Pro Gly Glu
        50                  55                  60

Lys Gly Glu Lys Gly Asp Pro Gly Leu Val Gly Pro Lys Gly Asp Thr
65                  70                  75                  80

Gly Glu Thr Gly Val Thr Gly Val Glu Gly Pro Arg Gly Phe Pro Gly
                85                  90                  95

Thr Pro Gly Arg Lys Gly Glu Pro Gly Glu Ser Ala Tyr Val His Arg
            100                 105                 110

Ser Ala Phe Ser Val Gly Leu Glu Ser Arg Ile Thr Val Pro Asn Val
        115                 120                 125

Pro Ile Arg Phe Thr Lys Ile Phe Tyr Asn Leu Gln Asn His Tyr Asp
    130                 135                 140

Gly Thr Thr Gly Lys Phe His Cys Asn Ile Pro Gly Leu Tyr Tyr Phe
145                 150                 155                 160

Ser Tyr His Ile Thr Val Tyr Leu Lys Asp Val Lys Val Ser Leu Tyr
                165                 170                 175

Lys Lys Asp Lys Ala Met Leu Phe Thr Tyr Asp Gln Tyr Gln Glu Lys
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Asp Gly Asp Ser Tyr Gly Ile
    210                 215                 220

Tyr Ala Asp Asn Val Asn Asp Ser Thr Phe Thr Gly Phe Leu Leu Tyr
225                 230                 235                 240

His Asp Thr Asn
```